(12) United States Patent
Gutierrez

(10) Patent No.: US 12,285,356 B2
(45) Date of Patent: Apr. 29, 2025

(54) PROGRAMMABLE THERAPEUTIC AGENT DELIVERY FROM EYE MOUNTED DEVICE

(71) Applicant: Verily Life Sciences LLC, Dallas, TX (US)

(72) Inventor: Christian Gutierrez, Pacifica, CA (US)

(73) Assignee: Verily Life Sciences LLC, Dallas, TX (US)

( * ) Notice: Subject to any disclaimer, the term of this patent is extended or adjusted under 35 U.S.C. 154(b) by 230 days.

(21) Appl. No.: 17/941,353

(22) Filed: Sep. 9, 2022

(65) Prior Publication Data
US 2023/0000677 A1 Jan. 5, 2023

Related U.S. Application Data

(63) Continuation of application No. 16/736,414, filed on Jan. 7, 2020, now Pat. No. 11,464,674.
(Continued)

(51) Int. Cl.
*A61F 9/00* (2006.01)
*A61N 1/32* (2006.01)
*G16H 20/17* (2018.01)

(52) U.S. Cl.
CPC ............ *A61F 9/0017* (2013.01); *A61N 1/325* (2013.01); *G16H 20/17* (2018.01)

(58) Field of Classification Search
CPC ........... A61B 3/00; A61B 5/03; A61B 5/4839; A61F 9/0017; A61N 1/30; A61N 1/325
See application file for complete search history.

(56) References Cited

U.S. PATENT DOCUMENTS 5,797,898 A 8/1998 Santini, Jr. et al.
6,154,671 A 11/2000 Parel et al.
(Continued)

FOREIGN PATENT DOCUMENTS

CN 107073233 A 8/2017
WO 2006/047788 5/2006
(Continued)

OTHER PUBLICATIONS

International Application No. PCT/US2020/012548, "Invitation to Pay Additional Fees and, Where Applicable, Protest Fee", Apr. 3, 2020, 16 pages.
(Continued)

*Primary Examiner* — Deanna K Hall
(74) *Attorney, Agent, or Firm* — Haynes and Boone, LLP

(57) ABSTRACT

The present disclosure relates to relates to systems and methods for on-demand delivery of a therapeutic agent from an eye mounted device. Particularly, aspects of the present invention are directed to a method of delivering a therapeutic agent, the method including receiving, at a controller of a therapeutic agent release and delivery device, a first command signal for delivery of a therapeutic agent based on a dosing time window. Upon receipt of the first command signal, the controller determines whether one or more compliance conditions are satisfied. When the one or more conditions are satisfied, the controller initiate a release and delivery protocol that commands a signal generator to generate and send a second command signal causing a capacitor or one or more circuits to deliver an actuation signal causing one or more therapeutic agent delivery mechanisms to open and release the therapeutic agent from one or more reservoirs.

20 Claims, 9 Drawing Sheets

Related U.S. Application Data

(60) Provisional application No. 62/790,310, filed on Jan. 9, 2019.

(56) References Cited

U.S. PATENT DOCUMENTS

| | | |
|---|---|---|
| 6,319,240 B1 | 11/2001 | Beck |
| 6,544,193 B2 | 4/2003 | Abreu |
| 8,529,538 B2 | 9/2013 | Pang et al. |
| 2002/0188282 A1 | 12/2002 | Greenberg |
| 2006/0088515 A1 | 4/2006 | Higuchi et al. |
| 2007/0123814 A1 | 5/2007 | Roy |
| 2007/0260171 A1 | 11/2007 | Higuchi et al. |
| 2008/0168921 A1 | 7/2008 | Uhland et al. |
| 2010/0256597 A1 | 10/2010 | Prausnitz et al. |
| 2011/0144619 A1 | 6/2011 | Meng et al. |
| 2014/0207048 A1 | 7/2014 | Dipierro et al. |
| 2014/0228783 A1 | 8/2014 | Kraft |
| 2016/0175148 A1 | 6/2016 | De Sousa Martins et al. |

FOREIGN PATENT DOCUMENTS

| | | |
|---|---|---|
| WO | 2007/050645 | 5/2007 |
| WO | 2009/086112 | 7/2009 |
| WO | 2016/118933 | 7/2016 |
| WO | 2018/064377 | 4/2018 |

OTHER PUBLICATIONS

International Preliminary Report on Patentability received for PCT Patent Application No. PCT/US20/12548, mailed on Jul. 22, 2021, 17 pages.
Non-Final Office Action received for U.S. Appl. No. 16/736,414, mailed on Jan. 20, 2022, 10 pages.
Notice of Allowance received for U.S. Appl. No. 16/736,414, mailed on Jun. 7, 2022, 8 pages.
Notice of Allowance received for U.S. Appl. No. 16/736,414, mailed on Jun. 22, 2022, 2 pages.
PCT International Search Report and Written Opinion for corresponding International Application Serial No. PCTUS2020/012552, dated Apr. 17, 2020, pp. 1-17.
PCT International Search Report and Written Opinion for corresponding International Application Serial No. PCT/US2020/012548, dated Jun. 24, 2020, pp. 1-23.
China National Intellectual Property Administration, Notice on the First Office Action, Application No. 202080020082.X, Aug. 8, 2024, 30 pages.

PROGRAMMABLE THERAPEUTIC AGENT DELIVERY FROM EYE MOUNTED DEVICE

CROSS-REFERENCE TO RELATED APPLICATION

The present application is a continuation application of U.S. patent application Ser. No. 16/736,414, filed 7 Jan. 2020, which claims the benefit of U.S. Provisional Application No. 62/790,310, filed 9 Jan. 2019. The entirety of these applications is hereby incorporated by reference by all purposes.

FIELD OF THE INVENTION

The present disclosure relates to delivery of a therapeutic agent, and more particularly to systems and methods for on-demand delivery of a therapeutic agent from an eye mounted device.

BACKGROUND

Medical treatment often requires the administration of a therapeutic agent (e.g., medicament, chemicals, small-molecule drugs, genes, etc.) to a specific area of the patient's body. A significant challenge that most therapeutic agents face is their inability to be delivered to the specific area in an effective manner. In traditional therapeutic agent delivery systems such as oral ingestion (e.g., solid or liquid forms), inhalants, or intravascular injection, the therapeutic agent is distributed systemically through the body via the circulatory, pulmonary, or lymphatic system. For most therapeutic agents, only a small portion of the agent reaches the specific area or diseased tissue to be affected, such as in chemotherapy where a substantial portion (e.g., about 99%) of the therapeutic agent administered to a patient does not reach the tumor site.

In contrast to traditional systemic delivery systems, targeted therapeutic agent delivery seeks to concentrate the agent in the area or tissues of interest while reducing the relative concentration of the agent in the remaining tissues. The goal of a targeted therapeutic agent delivery system is to prolong, localize, target and have a protected therapeutic agent interaction with the diseased tissue (specific part of the body). Some diseases, however, are difficult to treat with currently available therapies and/or require administration of drugs to anatomical regions to which access is difficult to achieve. A patient's eye is a prime example of a difficult-to-reach anatomical region, and many ocular diseases, including retinitis pigmentosa, age-related macular degeneration (AMD), diabetic retinopathy, and glaucoma, are difficult to treat with many of the currently available therapies.

Over the last several decades a multitude of approaches involving both therapeutic agent formulation and delivery system development have been undertaken to address these ocular diseases. Despite significant advances in the development of therapeutic agents, the currently available devices and systems for delivery of the therapeutic agents are limited to two primary routes of administration: 1) topical eye drops, and 2) intravitreal needle injection. Both of these administration options, while effective if regimens are strictly maintained, ultimately fail in providing long-term curative outcomes for patients, primarily due to deficiencies in maintaining localization of the therapeutic agent at the treatment site of the eye and a lack of compliance by the patient in administration of the therapeutic agent. Accordingly, improved methods of ocular therapeutic agent delivery are required to address the shortcomings of topical eye drops and intravitreal injections.

BRIEF SUMMARY

In various embodiments, a method is provided that comprises receiving, at a controller of a therapeutic agent release and delivery device, a first command signal for delivery of a dose of a therapeutic agent based on a dosing time window; upon receipt of the first command signal, the controller determines whether one or more compliance conditions are satisfied; when the one or more conditions are not satisfied, the controller determines whether the dosing time window is still active based on a therapy regimen; when the dosing time window is not still active, the controller skips delivery of the dose of the therapeutic agent and records the skip as a negative compliance event; and when the one or more conditions are satisfied, the controller initiate a release and delivery protocol that commands a signal generator to generate and send a second command signal causing a capacitor or one or more circuits to deliver an actuation signal causing one or more therapeutic agent delivery mechanisms to open and release the dose of the therapeutic agent from one or more reservoirs.

In some embodiments, the first command signal is received by the controller from an algorithm or data table stored in the controller or memory of the therapeutic agent delivery device. In some embodiments, a treatment protocol is stored in the algorithm or data table, which includes instructions for generating the first command signal to cause the delivery of the dose of the therapeutic agent in accordance with the dosing time window of a therapy regimen. In some embodiments, the one or more compliance conditions are stored in the controller or the memory of the therapeutic agent delivery device.

In some embodiments, the one or more compliance conditions include positioning of the therapeutic agent delivery device in contact with a target tissue, and the determining whether the one or more compliance conditions are satisfied includes determining whether the therapeutic agent delivery device is in contact with the target tissue. In some embodiments, the controller determines whether the dosing time window is still active by comparing a present time to time boundaries of the dosing time window in the therapy regimen.

Optionally, the method further includes recording, by the controller, the delivery of the dose of the therapeutic agent as a positive compliance event.

In some embodiments, the release and delivery protocol further includes commanding the signal generator to generate and send a third command signal causing the capacitor or the one or more circuits to deliver another actuation signal causing an iontophoretic electrode system to deliver the dose of the therapeutic agent into the target tissue using an electric field.

In various embodiments, a method is provided for comprising monitoring, at a controller of a therapeutic agent release and delivery device, a physiological parameter via one or more sensors connected to a target tissue; determining, by the controller, whether the physiological parameter is abnormal; when the physiological parameter is not abnormal, continuing to monitor, by the controller, the physiological parameter; and when the physiological parameter is abnormal, initiating, by the controller, a release and delivery protocol that commands a signal generator to generate and send a first command signal causing a capacitor or one or more circuits to deliver an actuation signal causing one or more therapeutic agent delivery mechanisms to open and release a dose of a therapeutic agent from one or more reservoirs.

In some embodiments, the physiological parameter is intraocular pressure. In some embodiments, the method further comprises obtaining and recording, by the controller, target or baseline values for the physiological parameter.

In some embodiments, the determining whether the physiological parameter is abnormal, comprises: (i) comparing values of the physiological parameter during the monitoring to the target or baseline values to determine a magnitude and direction of deviation error in the physiological parameter, and (ii) comparing the determined magnitude and direction of deviation error for the physiological parameter to predetermined threshold values or ranges of values set for the physiological parameter to determine whether an abnormal physiology is detected.

In some embodiments, the release and delivery protocol further includes commanding the signal generator to generate and send a second command signal causing the capacitor or the one or more circuits to deliver another actuation signal causing an iontophoretic electrode system to deliver the dose of the therapeutic agent into the target tissue using an electric field.

In some embodiments, the release and delivery protocol determines a type and the dose of the therapeutic agent to be released for a present situation based on a stored therapy regimen.

In some embodiments, the present situation is the detection of the abnormal physiological parameter and includes the measured magnitude and direction of deviation for the physiological parameter, and the release and delivery protocol initiated by the controller identifies the type and the dose of the therapeutic agent to be released specific for the measured magnitude and direction of deviation for the physiological parameter.

In various embodiments, a method is provided for that comprises: obtaining, by a controller of a therapeutic agent release and delivery device, one or more parameters set by a health care provider; monitoring, at the controller, a physiological parameter via one or more sensors connected to a target tissue; determining, by the controller, whether the physiological parameter is abnormal based on the one or more parameters set by the health care provider; when the physiological parameter is abnormal, obtaining, by the controller, a therapy regimen specific for a patient based on the one or more parameters, where the therapy regimen includes therapeutic agent classes, recommended dosing, and dosing time windows; determining, by the controller, whether the therapy regimen should be adjusted based on the monitoring of the physiologic parameter; when the therapy regimen should be adjusted, adjusting, by the controller, the therapy regimen based on: (i) the one or more parameters, and (ii) the monitoring of the physiologic parameter; and initiating, by the controller, a release and delivery protocol that commands a signal generator to generate and send a first command signal causing a capacitor or one or more circuits to deliver an actuation signal causing one or more therapeutic agent delivery mechanisms to open and release a dose of at least one therapeutic agent from one or more reservoirs, where the release and delivery protocol is selected by the controller based on the adjusted therapy regimen.

In some embodiments, the physiological parameter is intraocular pressure. In some embodiments, the one or more parameters include a therapeutic agent treatment hierarchy that includes multiple therapeutic agents, a maximum daily dosage for each therapeutic agent in the therapeutic agent treatment hierarchy, and one or more target or baseline profiles for the physiological parameter based on a patient's current medical state and treatment goals.

In some embodiments, the determining whether the physiological parameter is abnormal, comprises: (i) comparing values of the physiological parameter during the monitoring to target or baseline values from the one or more target or baseline profiles to determine a magnitude and direction of deviation error in the physiological parameter, and (ii) comparing the determined magnitude and direction of deviation error for the physiological parameter to predetermined threshold values or ranges of values set for the physiological parameter to determine whether an abnormal physiology is detected.

In some embodiments, the determining of whether the therapy regimen should be adjusted is based on the monitoring of the physiologic parameter, patient health factors, and personalization factors. In some embodiments, the controller adjusts the therapy regimen based on: (i) the one or more parameters, (ii) the monitoring of the physiologic parameter, and (iii) the patient health factors, the personalization factors, or a combination thereof.

In some embodiments, the release and delivery protocol further includes commanding the signal generator to generate and send a second command signal causing the capacitor or the one or more circuits to deliver another actuation signal causing an iontophoretic electrode system to deliver the dose of at least one therapeutic agent into the target tissue using an electric field.

BRIEF DESCRIPTION OF THE DRAWINGS

The present invention will be better understood in view of the following non-limiting figures, in which.

DETAILED DESCRIPTION

I. Introduction

The following disclosure describes systems and methods for on-demand delivery (active delivery) of a therapeutic agent from an eye mounted device. Various embodiments of systems and/or methods described herein are directed toward control methods, timing and algorithms for programmed targeted delivery of one or multiple therapeutic agents (different or same types). As used herein, the phrase "targeted" or "targeted delivery" refers to a technique of delivering a therapeutic agent to a subject in a localized manner that increases a concentration of the therapeutic agent at a treatment site of the subject relative to areas outside of the treatment site. As used herein, the term "controlled" or "controlled delivery" refers to a technique of delivering a therapeutic agent to a subject locally or systemically at a predetermined rate for a specified period of time. As used herein, the term "therapeutic agent" or "agent" comprises any desired pharmaceutical agent or mixture of individual pharmaceutical agents or the like, for the administration of one or more active agents to a region of a patient. In various embodiments, the devices or systems are designed to be placed on a surface (e.g., a corneal or scleral surface) of the eye for targeted and controlled delivery of a therapeutic agent to a treatment site of an eye. The devices or systems comprise reservoir(s) housing a therapeutic agent in one or more physical forms including aqueous (liquid), gel, dry (powder), or other combinations thereof. The reservoir(s) provide a means for temporary storage of the therapeutic agent prior to release and delivery to a treatment site. In some embodiments, the release and delivery of the therapeutic agent is actively, passively, or a combination thereof, controlled by one or more mechanisms to achieve fully customizable targeted therapeutic agent delivery regimes that drastically increase residence time of the therapeutic agent in the region of interest (e.g., the sclera, outer cornea, posterior segment, etc.) from about 30 seconds to greater than 30 minutes when compared to topical administration such as eye drops.

Figure 1A:
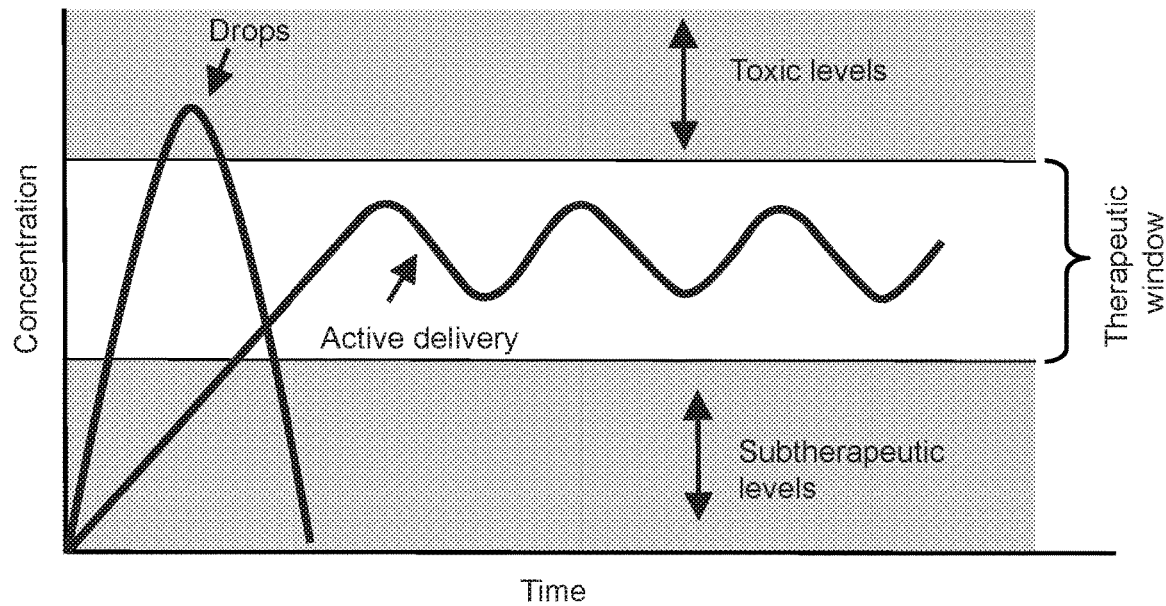
FIG. 1A shows a diagram depicting topical, injection, and active drug delivery modalities in accordance with various embodiments.
Figure 1B:
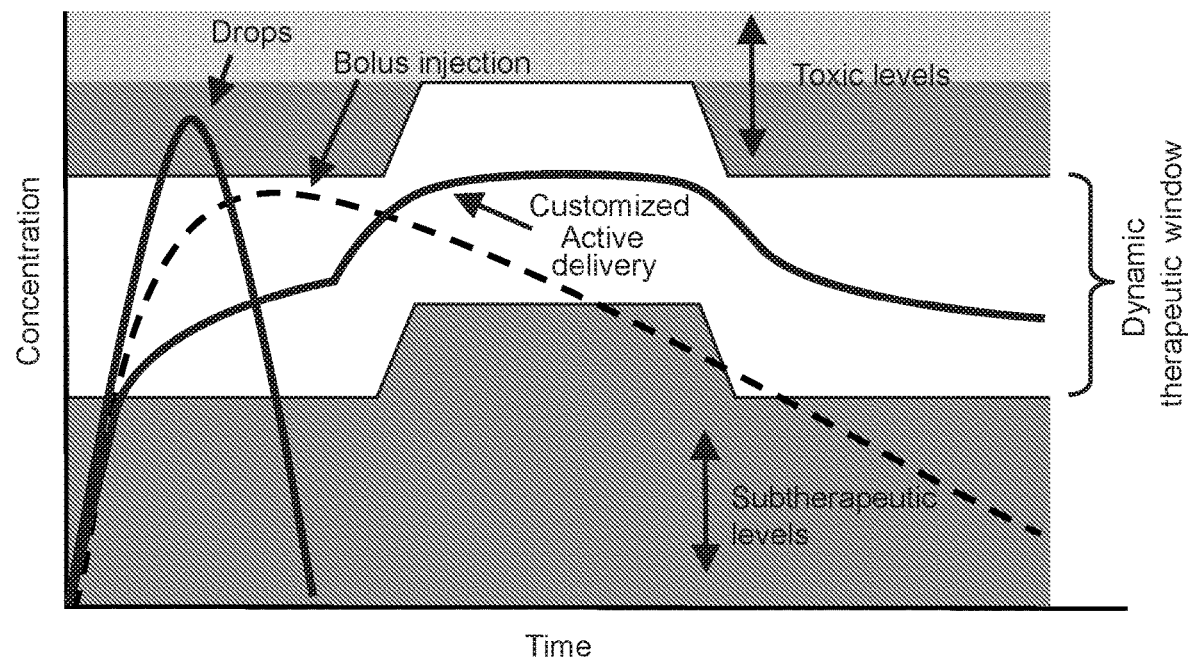
FIG. 1B shows a diagram depicting topical, injection, and active drug delivery modalities with a dynamic therapeutic window in accordance with various embodiments.

A problem associated with conventional systems and devices for targeted ocular therapeutic agent delivery (i.e., 1) topical eye drops and 2) intravitreal needle injection), is compliance and customized delivery profiles. For example, conventional systems and devices for targeted ocular therapeutic agent delivery ultimately fail in providing long-term curative outcomes for patients, primarily due to a lack of compliance, and assistive agent administration technologies that help patients achieve compliance are needed. Moreover, conventional systems and devices rely on patient assisted procedures (e.g., eye drops) or out-patient procedures (e.g., needle injections) with no active control of dosage or delivery, and thus lack the ability to implement patient-specific treatment. FIG. 1A shows a diagram depicting topical, injection, and active drug delivery modalities. Compared to conventional agent administration approaches, the active delivery is ideally suited to maintaining physiologically relevant concentrations in the therapeutic window. FIG. 1B shows a diagram depicting topical, injection, and active drug delivery modalities with a dynamic therapeutic window. Compared to conventional agent administration approaches, active delivery is the only method capable of maintaining physiologically relevant concentrations in conditions with a time-varying therapeutic window.

To address these problems, the present invention is directed to devices or systems that have a reservoir of therapeutic agent and one or more therapeutic agent delivery mechanisms for on-demand delivery of the therapeutic agent to a target region such as the vitreous humor. In some embodiments, the devices or systems provide the on-demand delivery of the therapeutic agent using an open control system or open-loop system where the output signal or condition is neither measured nor fed back for comparison with the input signal or system set point. For example, a burst or periodic release of a therapeutic agent from the one or more therapeutic agent delivery mechanisms can be triggered by a command signal. In other embodiments, the devices or systems provide the on-demand delivery of the therapeutic agent using a closed control system or closed-loop system (feedback control) where an open loop system is used as the forward path but one or more feedback loops or paths are included between the output signal and the input signal. For example, a burst or periodic release of a therapeutic agent from one or more therapeutic agent delivery mechanisms can be triggered based on one or more parameters obtained from one or more sensors. As used herein, when an action is "triggered by" or "based on" something, this means the action is triggered or based at least in part on at least a part of the something.

One illustrative embodiment of the present disclosure comprises: receiving, at a controller of a therapeutic agent release and delivery device, a first command signal for delivery of a dose of a therapeutic agent based on a dosing time window; upon receipt of the first command signal, the controller determines whether one or more compliance conditions are satisfied; and when the one or more conditions are satisfied, the controller initiateS a release and delivery protocol that commands a signal generator to generate and send a second command signal causing a capacitor or one or more circuits to deliver an actuation signal causing one or more therapeutic agent delivery mechanisms to open and release the dose of the therapeutic agent from one or more reservoirs.

Another illustrative embodiment of the present disclosure comprises: monitoring, at a controller of a therapeutic agent release and delivery device, a physiological parameter via one or more sensors connected to a target tissue; determining, by the controller, whether the physiological parameter is abnormal; and when the physiological parameter is abnormal, initiating, by the controller, a release and delivery protocol that commands a signal generator to generate and send a first command signal causing a capacitor or one or more circuits to deliver an actuation signal causing one or more therapeutic agent delivery mechanisms to open and release a dose of a therapeutic agent from one or more reservoirs.

Another illustrative embodiment of the present disclosure comprises: obtaining, by a controller of a therapeutic agent release and delivery device, one or more parameters set by a health care provider; monitoring, at the controller, a physiological parameter via one or more sensors connected to a target tissue; determining, by the controller, whether the physiological parameter is abnormal based on the one or more parameters set by the health care provider; when the physiological parameter is abnormal, obtaining, by the controller, a therapy regimen specific for a patient based on the one or more parameters, where the therapy regimen includes therapeutic agent classes, recommended dosing, and dosing time windows; determining, by the controller, whether the therapy regimen should be adjusted based on the monitoring of the physiologic parameter; when the therapy regimen should be adjusted, adjusting, by the controller, the therapy regimen based on: (i) the one or more parameters, and (ii) the monitoring of the physiologic parameter; and initiating, by the controller, a release and delivery protocol that commands a signal generator to generate and send a first command signal causing a capacitor or one or more circuits to deliver an actuation signal causing one or more therapeutic agent delivery mechanisms to open and release a dose of at least one therapeutic agent from one or more reservoirs, where the release and delivery protocol is selected by the controller based on the adjusted therapy regimen.

Advantageously, these approaches allow for on-demand therapeutic agent delivery capable of achieving fully customizable drug release regimes from first-order constant release profiles to on-demand pulsatile release (e.g., burst, periodic, or continuous), which delivers acceptable concentrations of agent to intraocular tissue safely, while minimizing the systemic exposure to the agent. Also advantageously, therapeutic agents may be multiplexed to deliver "cocktails of active agents" to a target tissue over a given therapeutic window. Further, the devices or systems described herein can make the therapeutic agent delivery personalized to each individual patient.

II. Therapeutic Agent Delivery Devices or Systems

Figure 2A:
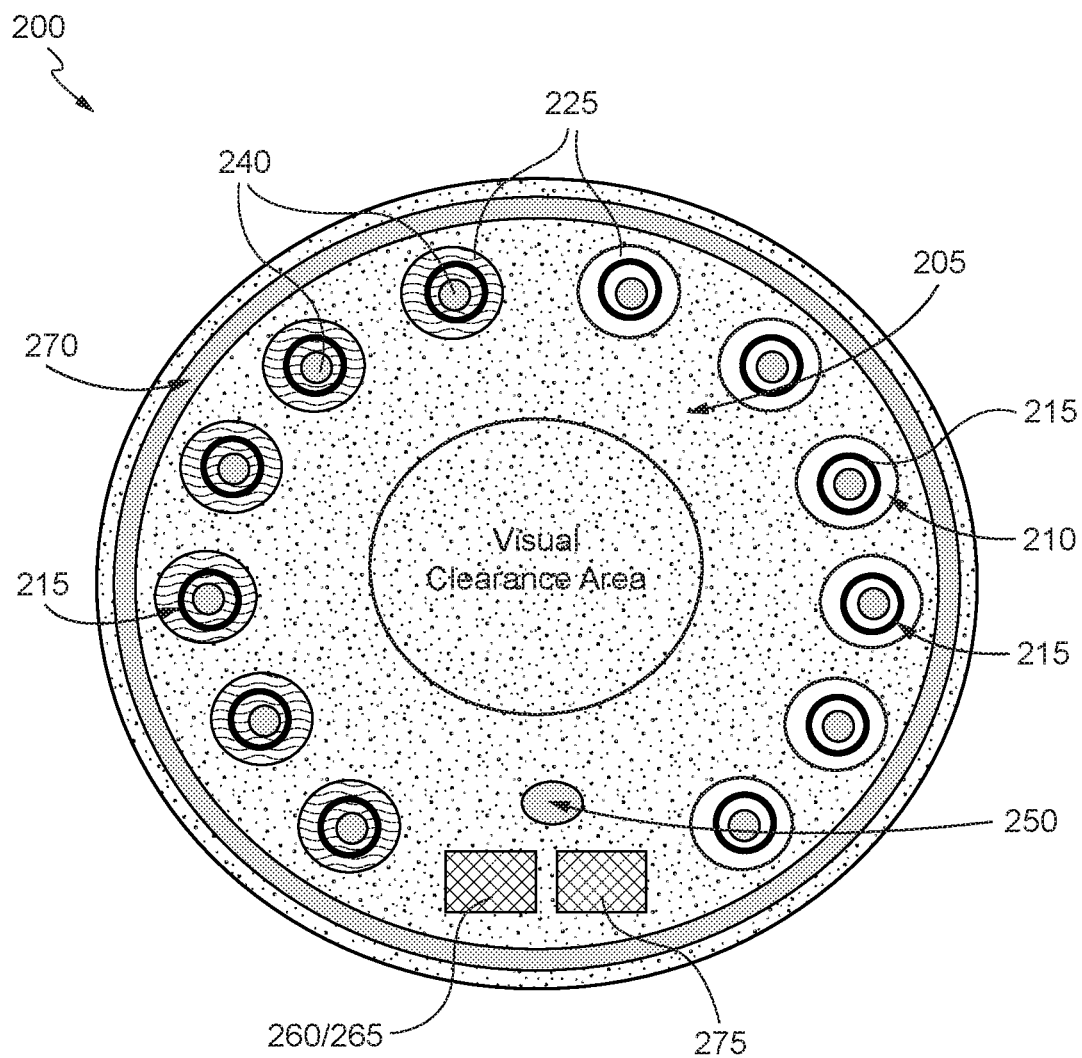
FIGS. 2A-2C show a therapeutic agent release device in accordance with various embodiments.
Figure 2B:
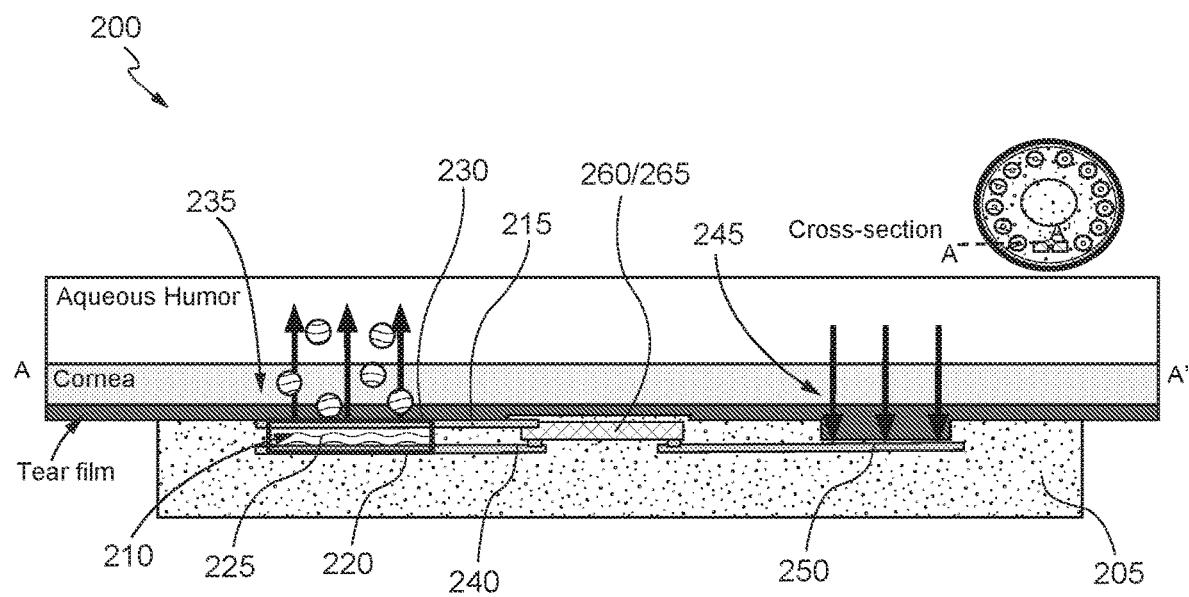

FIGS. 2A and 2B show a device 200 for therapeutic agent release in accordance with various embodiments. The device 200 includes a polymeric substrate 205 comprising one or more reservoirs 210 and one or more therapeutic agent delivery mechanisms 215. The polymeric substrate 205 may be formed of polyimide, liquid crystal polymer, parylene, polyether ether ketone, polyethylene terephthalate, poly (methyl methacrylate), polyurethane, rigid gas permeable fluorosilicone acrylate, a silicon-based polymer, a silicone acrylate, cyclic olefin co-polymer (COP/COC), a hydrogel, or a combination thereof. The polymeric substrate 205 has a shape and sufficient flexibility for mounting to the contour of the tissue such as the eye. In certain embodiments, the shape is a semi-circle shape. In other embodiments, the shape is a circle or donate shape (e.g., the shape of a contact lens), as shown in FIG. 2A.

In various embodiments, the one or more reservoirs 210 are integrated with or formed within the one or more layers of the polymer. The one or more reservoirs 210 may comprise a holding chamber 220 for a therapeutic agent 225 and an egress 230 for release of the therapeutic agent 225 from the holding chamber 220. The one or more reservoirs 210 are compatible with various physical forms of therapeutic agents including aqueous (liquid), gel, dry (powder), or other combinations thereof. In some embodiments, the one or more reservoirs 210 provide a means for temporary storage of one or more types of therapeutic agents 225 to allow for on-demand release and delivery of the therapeutic agents at a programmed time with a controlled rate thereby providing a therapeutic effect on the eye via transscleral absorption. In some embodiments, each reservoir 210 holds a single type of therapeutic agent 225 (same or different from other reservoirs). Type of therapeutic agent as used herein refers to the chemical make-up of the pharmaceutical agent or mixture of individual pharmaceutical agents or the like, the dose of the pharmaceutical agent or mixture of individual pharmaceutical agents or the like, or the combination of the chemical make-up and the dose. In other embodiments, each reservoir 210 holds multiple types of therapeutic agents 225 (same or different from other reservoirs). In other embodiments, a first type of therapeutic agent 225 is disposed within a first subset of the plurality of reservoirs 210 and a second type of therapeutic agent 225 is disposed within a second subset of the plurality of reservoirs 215. The one or more reservoirs 210 may have a volume from 0.01 nL to 100 μL, for example from 0.01 nL to 10 μL or about 1.0 μL, and stores a known quantity or volume of therapeutic agent. As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent. The one or more reservoirs 210 may be lined with a passive, hermetic, insulator, and/or inert coating such as a dielectric (e.g., $SiO_2$, $Al_2O_3$), or other approved agent-contacting material.

In various embodiments, the device 200 achieves release of the therapeutic agent 225 from the one or more reservoirs 210 to the tissue via the one or more therapeutic agent delivery mechanisms 215. In some embodiments, the one or more therapeutic agent delivery mechanisms 215 are active devices or a combination of active and passive devices. In some embodiments, the one or more reservoirs 210 comprises the holding chamber 220 for the therapeutic agent 225, the egress 230, and the active devices or combination of active and passive devices that temporarily blocks passage of the therapeutic agent 225 from the holding chamber 220 through the egress 230. In some embodiments, a single therapeutic agent delivery mechanism 215 is provided for each of the one or more reservoirs (same or different mechanism provide for each reservoir). In other embodiments, a plurality of therapeutic agent delivery mechanisms 215 are provided for each of the one or more reservoirs (same or different mechanisms provide for each reservoir). In other embodiments, a single therapeutic agent delivery mechanism 215 is provided for some of the one or more reservoirs, while a plurality of therapeutic agent delivery mechanisms 215 are provided for others of the one or more reservoirs (same or different mechanism(s) provide for each reservoir). While the arrangement of the therapeutic agent delivery mechanisms, reservoirs, and therapeutic agents are described herein in particular detail with respect to several described embodiments, it should be understood that other arrangements have been contemplated without departing from the spirit and scope of the present invention. For example, different arrangements of the therapeutic agent delivery mechanisms, reservoirs, and therapeutic agents are contemplated herein such that the release and delivery of a therapeutic agent(s) is targeted both temporally and spatially to a surface of the tissue (e.g., the scleral surface of the eye) where optimal therapeutic agent transfer into the tissue may occur.

In some embodiments, the one or more therapeutic agent delivery mechanisms 215 is active. As used herein, "active" means that an external stimulus is being applied to cause the opening/closing of the mechanism for release of the therapeutic agent. For example, the device 200 may achieve on-demand drug release through electronic control of at least one valve (therapeutic agent delivery mechanism 215) that is physically coupled to the one or more reservoirs 210 within the device 200. In certain embodiments, a circuit is formed on the polymeric substrate 205, and the circuit comprises a current source and at least one valve (the therapeutic agent delivery mechanism 215) such that a stimulus may be applied to open/close the at least one valve. A single reservoir may contain several "valves" which can be activated at selected times to increase the effective surface area available for diffusion to the tissue surface. This increases the effective dose provided at a given time. Alternatively, valves may be activated over time thereby maintaining a constant effective therapeutic dosage level over time. Alternatively, multiple discrete reservoirs with valves may be implemented, each with a discrete volume of drug for discretized bolus delivery.

The valves may be single use and opened on-demand electronically to allow therapeutic agent within the reservoir to pass through the valve opening towards the tissue, e.g., the scleral surface. Alternatively, the valves may be multi-use and opened/closed on-demand electronically to allow therapeutic agent within the reservoir to pass through the valve opening towards the tissue, e.g., the scleral surface. The valve opening action initiates therapeutic agent release into the thin post-device tear film located between the device and the sclera. The distance between the valve opening and the sclera is filled by the tear film (<20 µm), providing a short distance for a therapeutic agent to diffuse to the scleral surface. The combination of a thin tear film, subtarsal device placement and preferential therapeutic agent release to the scleral surface provides a quasi-static environment that promotes an increased therapeutic agent residence time (>30 minutes vs ~30 seconds for topical administration) and greater availability of therapeutic agent at the scleral surface, thus maximizing transscleral absorption and posterior segment bioavailability.

In certain embodiments, the therapeutic agent delivery mechanism 215 includes an active polymer device (or device constructed of a similar material). For example, an active polymer device may be used as a part of the control release mechanism to provide controlled release of the therapeutic agent 225 in constant doses over long periods, in accordance with first-order constant release profiles, or in accordance with on-demand pulsatile signals/commands. In some embodiments, the therapeutic agent may be encapsulated or provided behind a polymer membrane (e.g., encapsulated or closed off within the reservoir by a polymer layer that acts as a valve). The polymer membrane may be an environmentally-controlled device with the ability to undergo a physical or chemical behavioral change in response to an external stimulus. For example, a temperature or pH change may be used to trigger the behavioral change of the polymer but other stimuli, such as ultrasound, ionic strength, redox potential, electromagnetic radiation, and chemical or biochemical agents, may be used. Types of behavioral change can include transitions in solubility, hydrophilic-hydrophobic balance, and conformation. Upon receiving the stimuli and undergoing the behavior change, the environmentally-controlled device may release the therapeutic agent from the reservoir(s). The polymer for the environmentally-controlled device may include hydrogels, micelles, polyplexes, polymer-drug conjugates, or combinations thereof. Hydrogels are hydrophilic (co)polymeric networks capable of imbibing large amounts of water or biological fluids. Physical or covalent crosslinks may render hydrogels insoluble in water. Various hydrogels can be engineered in accordance with aspects of the present invention to respond to numerous stimuli.

In certain embodiments, the therapeutic agent delivery mechanism 215 includes an active metal device (or device constructed of a similar material). For example, an active metal device may be used as a part of the control release mechanism to provide controlled release of the therapeutic agent 225 in constant doses over long periods, in accordance with first-order constant release profiles, or in accordance with on-demand pulsatile signals/commands. In some embodiments, the therapeutic agent may be encapsulated or provided behind a metallic film (e.g., encapsulated or closed off within the reservoir by a metal layer that acts as a valve). Therapeutic agent release may be activated electronically through application of a potential or low-level voltage stimulus to a metallic thin film comprising the valve. In some embodiments, the thin film forms a seal on a side of the reservoir, which may be positioned against the tissue (see, e.g., FIG. 2B). The metallic film undergoes electrodissolution when a potential is applied under presence of the environmental fluid (e.g., a tear film). The release mechanism may be described through the following equilibrium equations (1) $Au + 2Cl^- \leftrightharpoons (AuCl_2^-)ads + e$ and (2) $(AuCl_2^-)ads \rightarrow AuCl_2^-$ (soln) with the rate limiting step being the activated desorption of the gold complex from the surface.

In some embodiments, gold is used as the metal film material because it is easily deposited and patterned, has a low reactivity with other substances and resists spontaneous corrosion in many solutions over the entire pH range. Gold has also been shown to be a biocompatible material. However, the presence of a small amount of chloride ion, as is naturally found in tear fluid, creates an electric potential region which favors the formation of soluble gold chloride complexes. Holding the anode potential in this corrosion region between 0.8 and 1.2 V, for example at about 1.0 V, enables reproducible gold dissolution of films having a thickness of between about 50 nm and about 500 nm. Potentials below this region are too low to cause appreciable corrosion, whereas potentials above this region result in gas evolution and formation of a passivating gold oxide layer that causes corrosion to slow or stop. Other metals such as copper or titanium tend to dissolve spontaneously under these conditions or do not form soluble materials on application of an electric potential. Although gold is used in some embodiments, it should understood that other materials may be used to achieve similar electrodissolution-mediated agent release.

In some embodiments, the therapeutic agent delivery mechanism 215 includes a combination of one or more passive devices and one or more active devices. In certain embodiments, the therapeutic agent delivery mechanism 215 is a passive polymer device (or device constructed of a similar material) and an active polymer or metal device. For example, an active polymer or metal device may be used as a part of the control release mechanism to provide controlled release of the therapeutic agent 225 from the one or more reservoirs 210. The therapeutic agent 225 may be encapsulated or provided behind a polymeric or metallic layer (e.g., encapsulated or closed off within the reservoir by a polymeric or metallic layer that acts as a valve). Once the active polymer or metal device is opened via external stimulus, the therapeutic agent 225 may be released out of the holding chamber 220 through the egress 230 into a passive polymer device such a polymeric matrix or hydrogel. Once the therapeutic agent 225 passes through the passive polymer device (e.g., via diffusion or osmotic pump), the therapeutic agent 225 may be released and delivered to a surface of a target tissue (e.g., the scleral surface). Alternatively, a passive polymer device may be used as a part of the control release mechanism to provide controlled release of the therapeutic agent 225 from the one or more reservoirs 210. The therapeutic agent 225 may be encapsulated or provided behind a polymeric layer (e.g., encapsulated or closed off within the reservoir by a polymeric layer that acts as a valve). Once the therapeutic agent 225 passes through the passive polymer device (e.g., via diffusion or osmotic pump), the therapeutic agent 225 may be released out of the holding chamber 220 through the egress 230 into an active polymer or metal device such as encapsulated or provided behind a polymeric or metallic layer. Once the active polymer or metal device is opened via external stimulus, the therapeutic agent 225 may be released and delivered to a surface of a target tissue (e.g., the scleral surface).

In some embodiments, the therapeutic agent delivery mechanism 215 includes an iontophoretic electrode system to facilitate delivery of the therapeutic agent 225 into the tissue. Iontophoresis is a local non-invasive technique in which an electric field is applied to enhance ionized therapeutic agent penetration into tissue. In certain embodiments, an iontophoretic electrode system such as an Ag—Ag/Cl electrode system is used for its ability to maintain local pH levels and eliminate soluble bulk electrode species. However, the iontophoretic electrode system may comprise other electrode materials such as platinum, platinum/iridium (PtIr) and alloys thereof, carbon, zinc/zinc chloride, gold, other suitable insoluble and inert metals that resist electrodissolution in solution over a given pH range, and combinations thereof. The anodal chamber contains an ionizable therapeutic agent D+ with its counter-ion A− and NaCl (tear film). Application of an electric potential to a electrode (e.g., an anode) causes a current to flow through the circuit. At the electrode solution interface, the Ag+ and Cl− react to form insoluble AgCl which is deposited on the electrode surface. Electromigration transports the cations, including the ionizable agent D+, from the anodal compartment and into the tissue. At the same time, endogenous anions, primarily Cl−, move into the anodal compartment. In the cathodal chamber, Cl− ions are released from an electrode (e.g., a cathode) surface and electroneutrality requires that either an anion is lost from the cathodal chamber or that a cation enters the cathodal chamber from the tissue. The extent and penetration depth of iontophoretic delivery is related to the electric field and the duration of application.

In some embodiments, the iontophoretic electrode system includes one or more chambers or compartments 235 (e.g., an anode chamber) that comprise a first iontophoresis electrode 240 (e.g., an anode) for transport of the therapeutic agent 225 from a release point of the active devices or combination of active and passive devices into a target tissue (e.g., the vitreous humor) via electromigration. In certain embodiments, the first iontophoresis electrode 240 is located under the one or more reservoirs 210 formed within the polymeric substrate 205. Moreover, at least a portion of the one or more chambers or compartments 235 is exposed to an environment external to the polymeric substrate 205. The one or more chambers or compartments 235 are capable of receiving the therapeutic agent 225 from the reservoir upon release of the therapeutic agent 225 via the active or combination of active and controlled release devices. The therapeutic agent 225 may be ionizable, and a counter ion (the counter ion has a charge opposite that of the therapeutic agent 225) may be disposed within the one or more reservoirs 210 or the one or more chambers or compartments 235. In embodiments in which multiple types of therapeutic agents are used, multiple types of counter ions may also be used (e.g., a first type of therapeutic agent may be ionized and a first type of counter ion has a charge opposite that of the first type of therapeutic agent and a second type of therapeutic agent may be ionized and the second type of counter ion has a charge opposite that of the second type of therapeutic agent. The iontophoretic electrode system further includes one or more chambers or compartments 245 (e.g., a cathode chamber) that comprise a second iontophoresis electrode 250 (e.g., a cathode) for maintaining electroneutrality within the tissue (e.g., the sclera). In some embodiments, one or more chambers or compartments 245 are formed within the one or more layers of polymer and at least a portion of one or more chambers or compartments 245 is exposed to an environment external to the polymeric substrate 205.

Figure 2C:
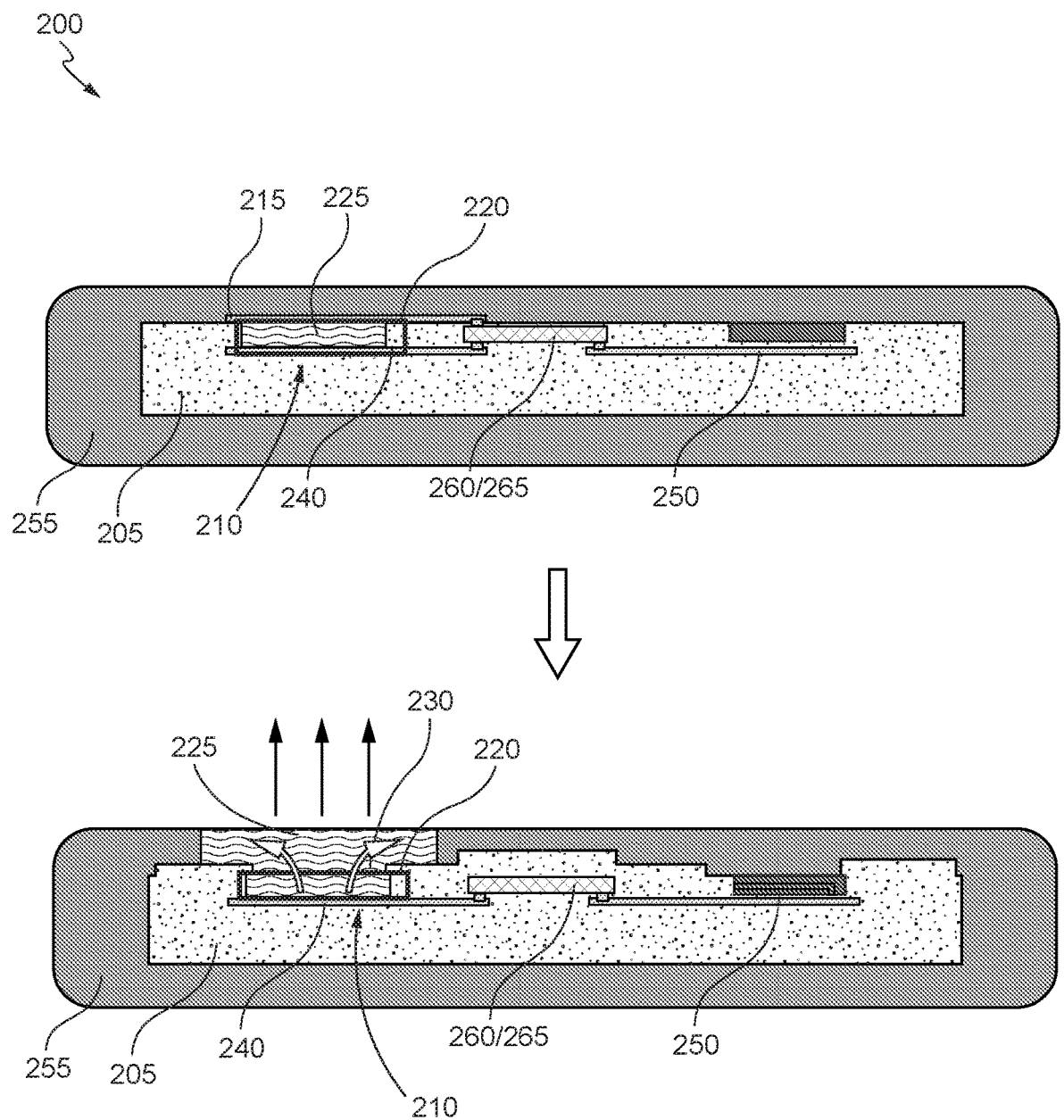

As shown in FIG. 2C, the device 200 may further include an overmold polymeric layer 255 formed around substantially an entirety of the polymeric substrate 205. In some embodiments, the polymeric substrate 205 is fully encapsulated by the overmold polymeric layer 255. The overmold polymeric layer 255 may be formed of polymethylmethacrylate, polyhydroxyethylmethacrylate, a hydrogel, a silicon-based polymer, a silicone elastomer, or a combination thereof. In certain embodiments, the overmold polymeric layer 255 has a water content between 30% and 50%, for example about 45% water content. In some embodiments, the therapeutic agent delivery mechanism 215 is a combination of active device(s) (e.g., a polymeric or metallic active device and the iontophoretic electrode system) and the overmold polymer layer 255 (a polymeric passive device). The therapeutic agent 225 may be encapsulated or provided behind the polymeric or metallic active device (e.g., encapsulated or closed off within the reservoir by a metallic layer that acts as a valve). Once the polymeric or metallic active device is opened via external stimulus and dissolution, the therapeutic agent 225 may be released out of the holding chamber 220 of the reservoir 210 through the egress 230 into the overmold polymeric layer, as shown in FIG. 2C. Once the therapeutic agent 225 passes through the passive polymer device (e.g., via diffusion or osmotic pump), the therapeutic agent 225 may be released and delivered to a surface of a target tissue (e.g., the scleral surface) via the iontophoresis electrode system including the first electrode 240 and the second electrode 250. This mechanism for release and delivery of the therapeutic agent may be used to achieve agent release kinetics similar to passive load-and-release drug-eluting approaches albeit with a fully-programmable and customizable active release and delivery initiation.

In other embodiments, the device 200 includes exposed access points or openings in the overmold polymeric layer 255 (e.g., hydrogel), which exposes a surface of the one or more reservoirs 210. In these embodiments, the post-device tear film or tissue is in direct contact with the therapeutic agent delivery mechanism 215 or the egress 230 of the reservoir 210. The term "direct" or "directly", as used herein, may be defined as being without something in between. The term "indirect" or "indirectly", as used herein, may be defined as having something in between. Upon release of the therapeutic agent 225 from the chamber 220, the therapeutic agent 225 permeates directly into the post-device tear film or tissue with facilitated delivery from the iontophoresis electrode system including the first electrode 240 and the second electrode 250. This mechanism for release and delivery may be used to achieve alternative release kinetics with fully-programmable and customizable active release and delivery similar to topical application of eye drops however with the benefit of drastically increased residence times, increased bioavailability and minimal drug loss. More generally, the device 200 enables customized delivery profiles which is currently unavailable with either topical eye drops or intravitreal needle injection. Advantageously, where the therapeutic window changes or is cyclic (e.g., due to circadian rhythm such as in glaucoma), the device 200 is able to meet these changes in a fully customized manner.

The device 200 may further include a power source 260, a capacitor 265, a communications device 270 (e.g., a WiFi antenna), and an electronics module 275 (i.e., hardware, software or a combination thereof). In some embodiments, the power source 260, the capacitor 265, the communications device 275, and the electronics module 280 are integrated with or formed within the one or more layers of the polymer. In other embodiments the power source 260, the capacitor 265, the communications device 270, and the electronics module 275 are formed on a top surface of the one or more layers of the polymer, e.g., formed on a proximal surface. In other embodiments, the power source 260, the capacitor 265, the communications device 270, and the electronics module 275 are formed on a separate polymeric substrate integrated with the substrate 205. In yet other embodiments, the power source 260, the capacitor 265, the communications device 270, and the electronics module 275 are formed within a housing integrated with the substrate 205 and/or a separate substrate. The housing may be comprised of materials that are biocompatible such as polymers, bioceramics or bioglasses for radio frequency transparency, or metals such as titanium.

The power source 260 may be connected (e.g., electrically connected) to the electronics module 275 to power and operate the components of the electronics module 275. The power source 260 may be connected (e.g., electrically connected) to the capacitor 265 to power and provide current flow for one or more circuits 280. The communications device 270 may be connected (e.g., electrically connected) to the electronics module 275 for wired or wireless communication with external devices via, for example, radiofrequency (RF) telemetry or WiFi. The electronics module 275 may be connected (e.g., electrically connected) to the capacitor 265 and the one or more circuits 280 such that the electronics module 275 is able to apply a signal or electrical current to electronic components such as gates, electrodes, or sensors connected to the one or more circuits 280. The electronics module 275 may include discrete and/or integrated electronic circuit components (e.g., one or more processors) that implement analog and/or digital circuits capable of producing the functions attributed to the device 200 such as applying a potential to one or more therapeutic agent delivery mechanisms 215, applying a potential to a circuit, or applying a potential to one or more electrodes. In various embodiments, the electronics module 275 may include software and/or electronic circuit components such as a signal generator that generates a signal causing the capacitor 265 or the one or more circuits 280 to deliver a voltage, potential, current, optical signal, or ultrasonic signal to electronic components, a controller that determines or senses signals either received from external devices via the communications device 270 or via electrodes or sensors connected to the one or more circuits 280, controls release and delivery parameters of the device 200, and/or causes release and delivery of the therapeutic agent 225 via the one or more reservoirs 210, and a memory with program instructions operable on by the signal generator and the controller to perform one or more processes for releasing or delivering the therapeutic agents 225.

While the device 200, the therapeutic agent delivery mechanisms 215 and electronics module 275 are described herein as a single wearable ocular unit with respect to several described embodiments, it should be understood that various systems and arrangements comprising the device 200, the therapeutic agent delivery mechanisms 215, and electronics module 275 are contemplated without departing from the spirit and scope of the present disclosure. For example, the device 200 may include the therapeutic agent delivery mechanisms 215 and electronics module 275 within a distributed environment such as a cloud computing environment, and the device 205, the one or more therapeutic agent delivery mechanisms 215, and electronics module 275 may be in communication via one or more communication networks. Examples of communication networks include, without restriction, the Internet, a wide area network (WAN), a local area network (LAN), an Ethernet network, a public or private network, a wired network, a wireless network, and the like, and combinations thereof.

Figure 3:
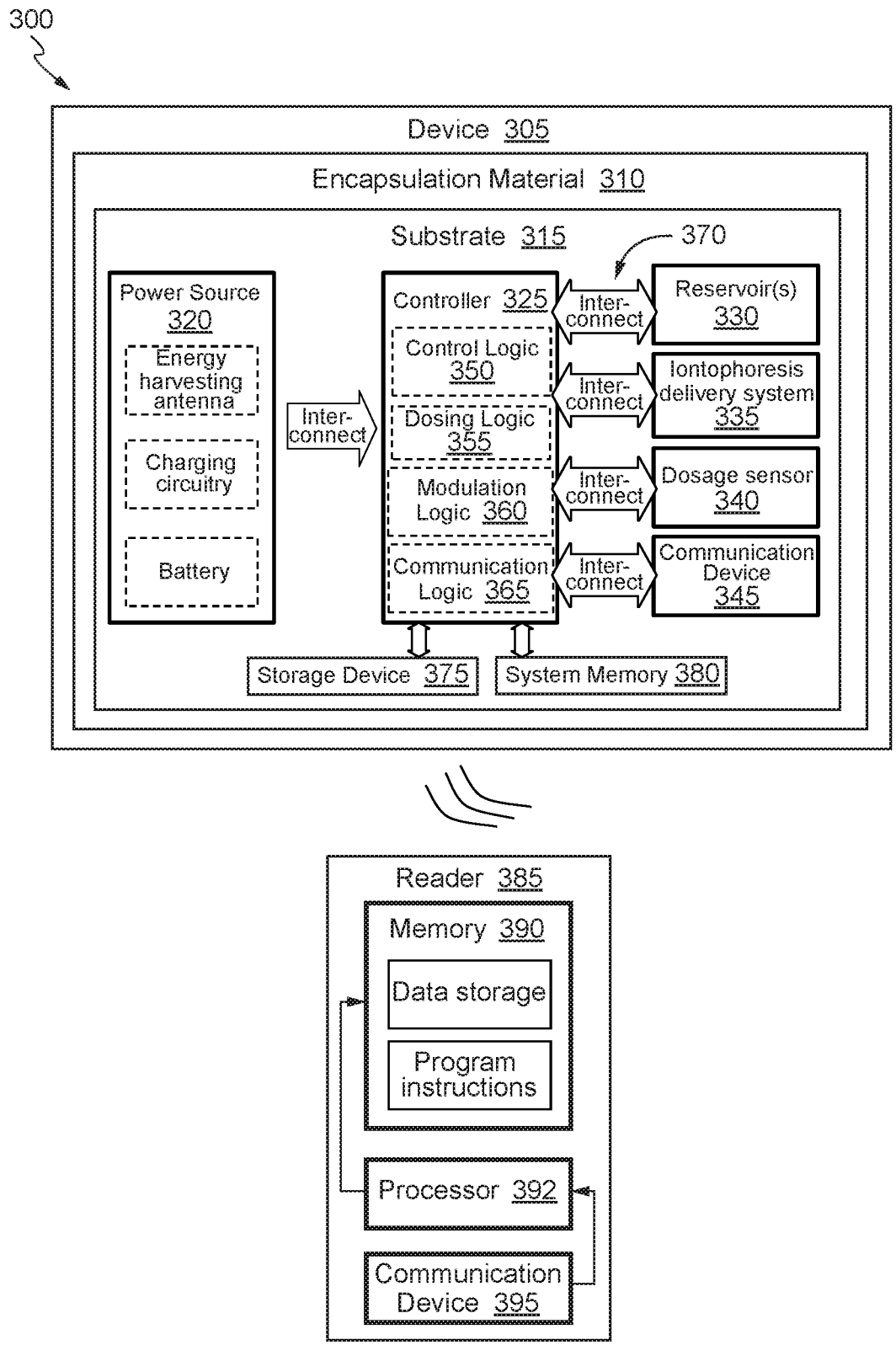
FIG. 3 shows a system for therapeutic agent release and delivery in accordance with various embodiments.

FIG. 3 shows a therapeutic agent release and delivery system 300 in accordance with various embodiments. In some embodiments, the therapeutic agent release and delivery system 300 includes one or more delivery devices 305 (e.g., device 200 described with respect to FIGS. 2A-2C), an optional encapsulation layer 310, and a substrate 315. In certain embodiments, the therapeutic agent release and delivery system 300 is disposed on one or both eyes of a patient. The substrate 315 includes software and/or electronic circuit components that may provide active or customized on-demand iontophoretic transscleral or transcorneal therapeutic agent delivery. The software and/or electronic circuit components includes a power source 320 (e.g., power source 260 described with respect to FIGS. 2A-2C), a controller 325 (e.g., electronics module 275 described with respect to FIGS. 2A-2C), the one or more reservoirs 330, the iontophoresis electrode delivery system 335, one or more sensors 340, and the communications device 345.

In certain embodiments, the controller 325 includes one or more conventional processors, microprocessors, or specialized dedicated processors that include processing circuitry operative to interpret and execute computer readable program instructions, such as program instructions for controlling the operation and performance of one or more of the various other components of device 305 for implementing the functionality, steps, and/or performance of the present embodiments. In certain embodiments, the controller 325 interprets and executes the processes, steps, functions, and/or operations of the present invention, which may be operatively implemented by the computer readable program instructions. For example, the controller 325 includes control logic 345, dosing logic 350, modulation logic 355, and communication logic 360 that communicate interactively via one or more circuits 365 with the one or more reservoirs 330, the iontophoresis electrode delivery system 335, the one or more sensors 340, and the communications device 345. In some embodiments, the information obtained or generated by the controller 325, e.g., the status of agent delivery, agent dosages, temporal location in therapeutic window, etc., can be stored in the storage device 370.

The storage device 370 may include removable/non-removable, volatile/non-volatile computer readable media, such as, but not limited to, non-transitory machine readable storage medium such as magnetic and/or optical recording media and their corresponding drives. The drives and their associated computer readable media provide for storage of computer readable program instructions, data structures, program modules and other data for operation of the controller 325 in accordance with the different aspects of the present invention. In some embodiments, the storage device 370 stores an operating system, application programs, and program data.

A system memory 375 may include one or more storage mediums, including for example, non-transitory machine readable storage medium such as flash memory, permanent memory such as read-only memory ("ROM"), semi-permanent memory such as random access memory ("RAM"), any other suitable type of non-transitory storage component, or any combination thereof. In some embodiments, an input/output system (BIOS) including the basic routines that help to transfer information between the various other components of device 305, such as during start-up, may be stored in the ROM. Additionally, data and/or program modules, such as at least a portion of operating system, program modules, application programs, and/or program data, that are accessible to and/or presently being operated on by one or more processors, may be contained in the RAM. In embodiments, the program modules and/or application programs can comprise, for example, control logic 345, dosing logic 350, modulation logic 355, and communication logic 360, which provides the instructions for execution of the one or more processors.

The communication device 345 may include any transceiver-like mechanism (e.g., a network interface, a network adapter, a modem, or combinations thereof) that enables device 305 to communicate with remote devices or systems, such as a mobile device or other computing devices such as, for example, a server in a networked environment, e.g., cloud environment. For example, device 305 may be connected to remote devices or systems via one or more local area networks (LAN) and/or one or more wide area networks (WAN) using communication device 845.

The controller 325 can be remotely accessed following implant through an external programmer or reader 345, such as an external computing device. For example, the external programmer or reader 345 can be used by healthcare professionals to check and program the controller 325 before or after distribution to a patient (e.g., while the patient is wearing the device 305), adjust release and delivery parameters during a delivery process, e.g., providing an initial set of the release and delivery parameters, and read any data concerning dosage, delivery, and compliance of the device during or after a dosing regimen. In some embodiments, the external programmer or reader 345 comprises a memory 350 (e.g., a storage device or system memory), one or more processors 355, and a communications device such as a WiFi antenna. The external programmer or reader 345 may communicate with the controller 325 via wired or wireless communication methods, such as, e.g., wireless radio frequency transmission.

As discussed herein, the system 300 may be configured to control release of a therapeutic agent from one or more reservoirs into a delivery region, and control application of a potential to a circuit to create a current flowing through the circuit that causes electromigration of the therapeutic agent from the delivery region to a tissue. In particular, device 300 may perform tasks (e.g., process, steps, methods and/or functionality) in response to controller 325 executing program instructions contained in non-transitory machine readable storage medium, such as system memory 375. The program instructions may be read into system memory 375 from another computer readable medium (e.g., non-transitory machine readable storage medium), such as data storage device 370, or from another device such as external programmer or reader 345 via the communication device 345 or server within or outside of a cloud environment. In some embodiments, an operator may interact with external programmer or reader 345 via one or more input devices and/or the one or more output devices to facilitate performance of the tasks and/or realize the end results of such tasks in accordance with various aspects described herein. In additional or alternative embodiments, hardwired circuitry may be used in place of or in combination with the program instructions to implement the tasks, e.g., steps, methods and/or functionality, consistent with the different aspects. Thus, the steps, methods and/or functionality disclosed herein can be implemented in any combination of hardware circuitry and software.

III. Methods for Delivering Therapeutic Agents

Figure 4:
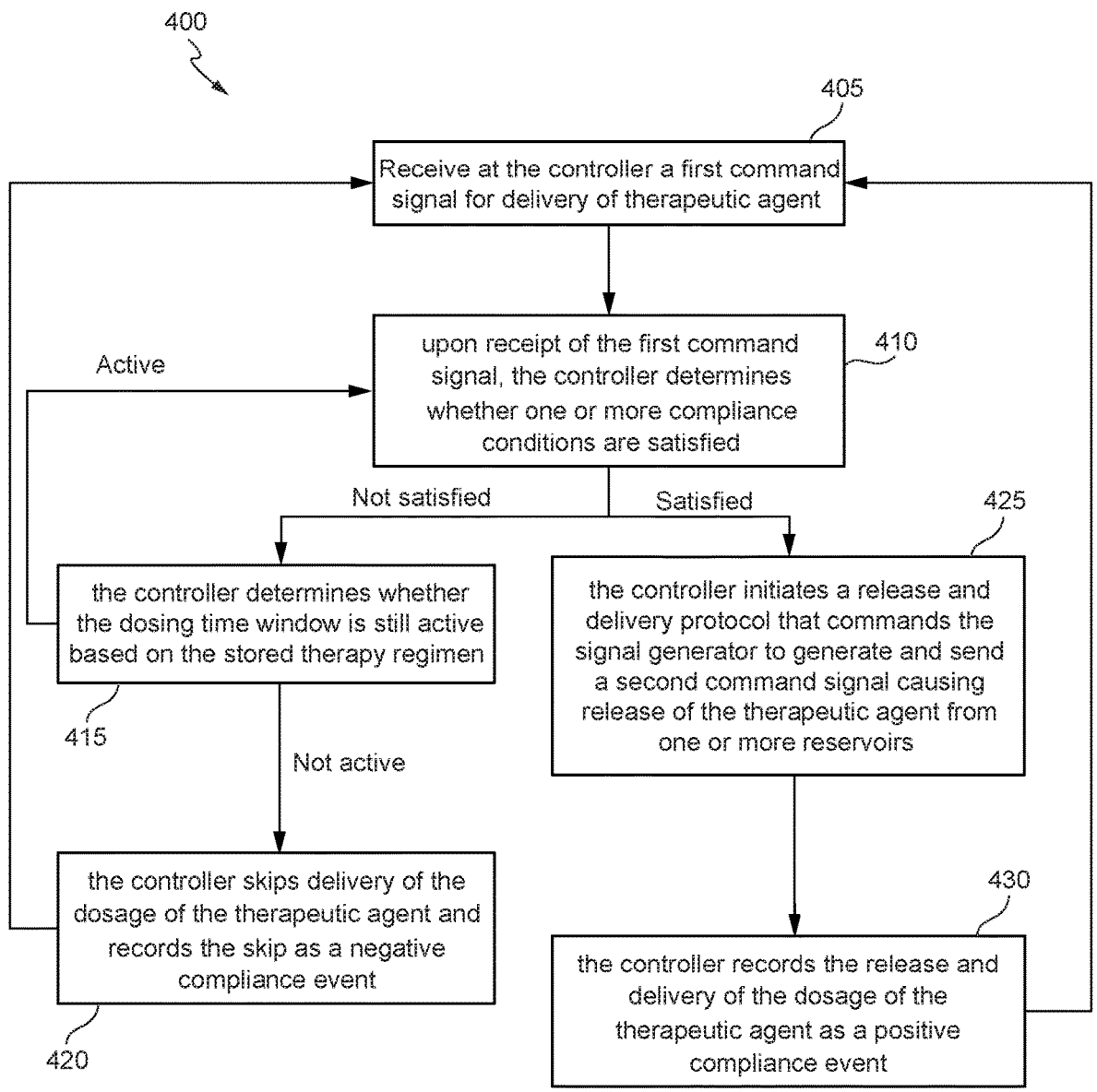
FIGS. 4-6 show exemplary flows for providing therapy in accordance with various embodiments.
Figure 5:
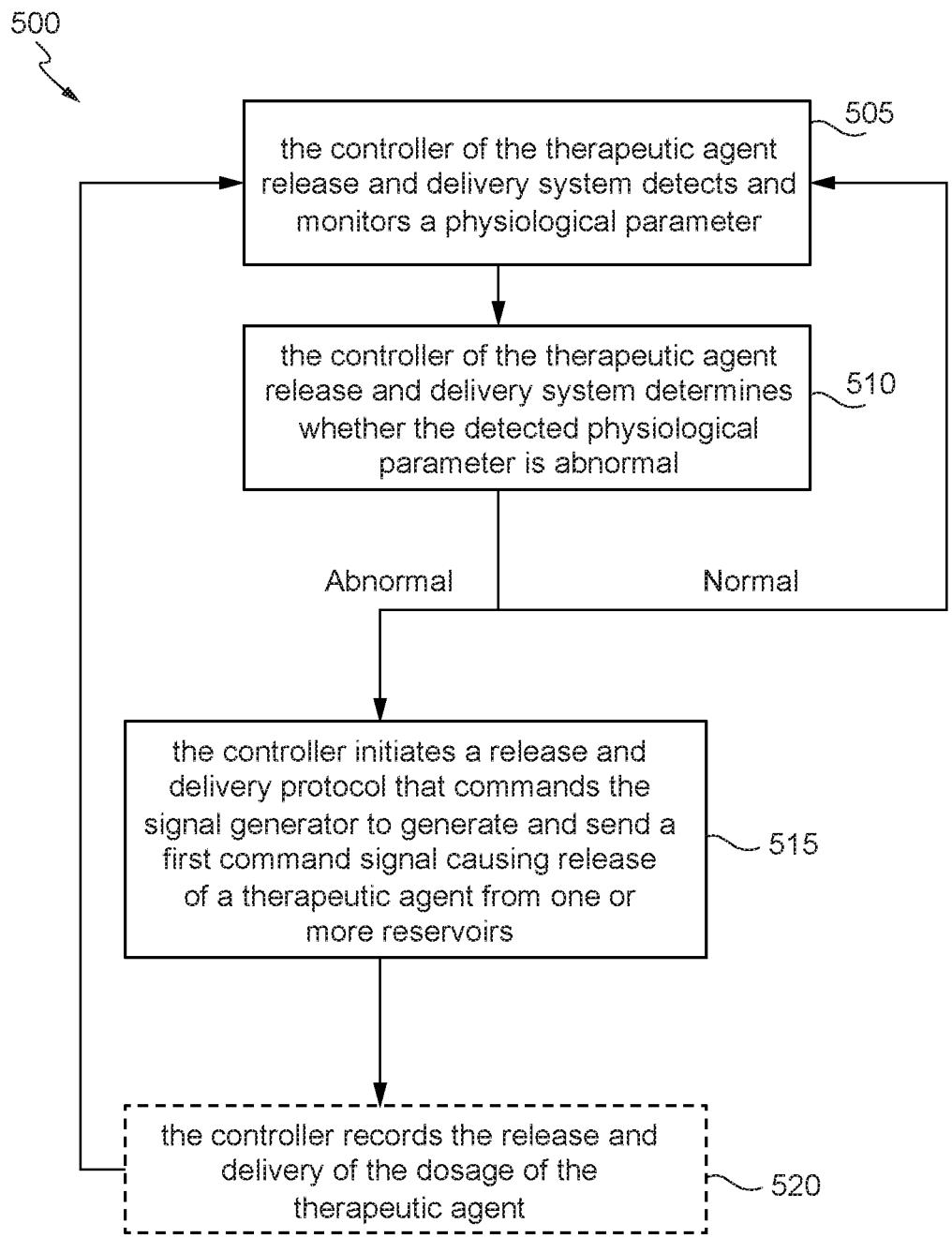
Figure 6:
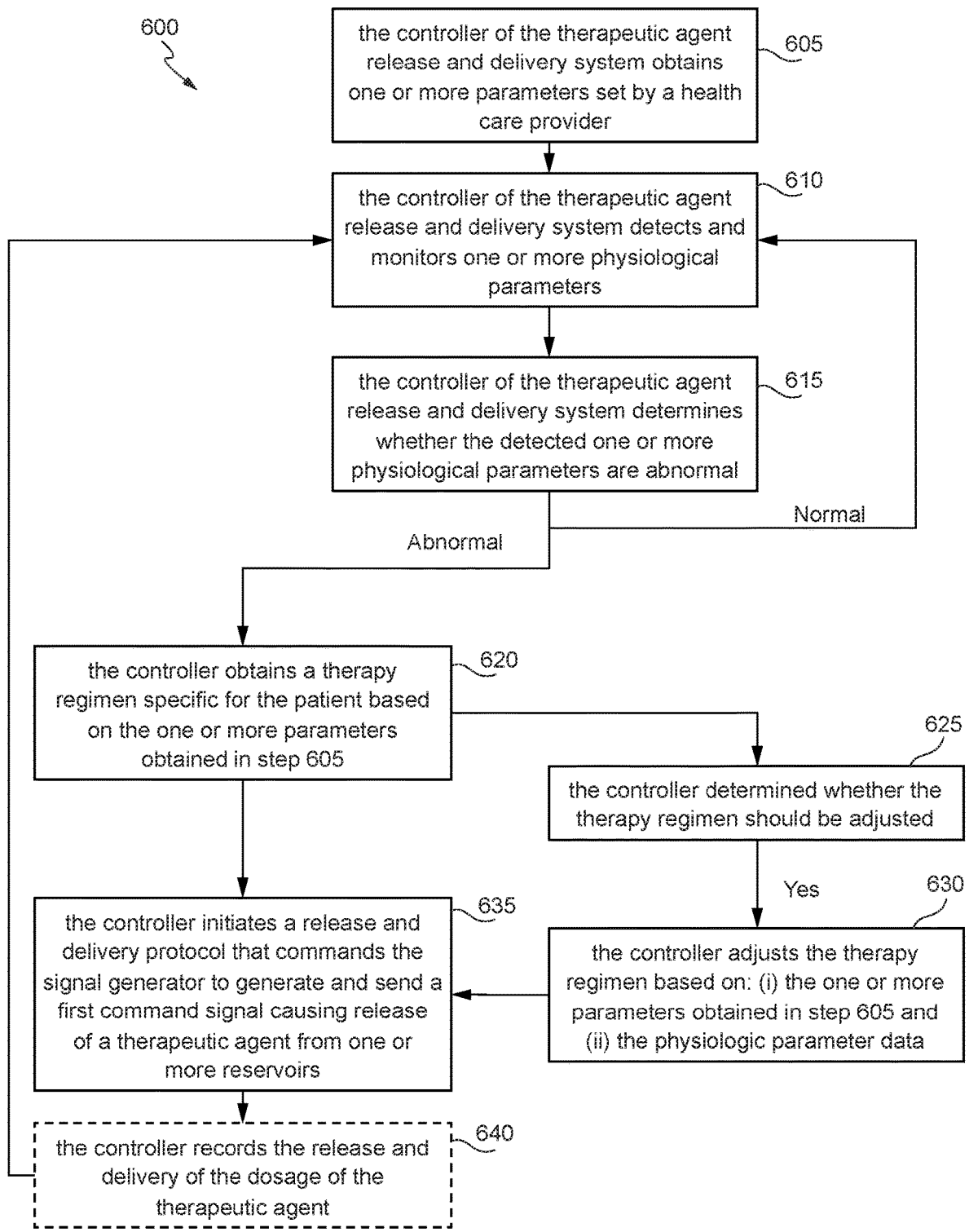

FIGS. 4-6 depict simplified flowcharts depicting processing performed for on-demand therapeutic agent release and delivery according to embodiments of the present invention. In some embodiments, dosing of multiple therapeutic agents discretely or in combination is enabled through electronically controlled agent release and delivery (e.g., via one or more therapeutic agent delivery mechanisms). The agent release and delivery may be programmed to follow one or more delivery profiles that can be specified by an administrator (e.g., a health care provider) to adhere to one or more dosing regimens. For example, standard dosing schedules currently used in clinical practice for the treatment of glaucoma are shown in Table 1. This is only for illustrative purposes as other diseases/conditions may require their own specific dosing schedules and are contemplated by the present embodiments. Each drug class targets a unique mechanism of action in the treatment of glaucoma (e.g., aqueous humour production vs ocular drainage), and the drug classes can be used individually (monotherapy) or in combination (e.g., bi-, tri-, quad-therapy) when the biological effects of multiple agents are understood to be additive. The specific times suggested may be tailored to the individual user so long as the health care provider recommended dosing regimen is adhered to by the user. Therefore customized or programmed release and delivery profiles can be specified for a single therapy regimen such as delivery of beta-blockers up to two times each day, which may then be executed by the processes described with respect to FIGS. 4-6.

TABLE 1

| Drug Class | Recommended Dosing | Exemplary Device Programmed Regimen |
|---|---|---|
| Prostaglandin analogues | One drop per day | 7 PM |
| Beta-blockers | Up to two drops per day | 10 AM and (7 PM based on provider assessment) |
| Alpha-agonists | Two or three drops per day | 10 AM, 7 PM, and (2 PM based on provider assessment) |
| Carbonic anhydrase inhibitors | Two or three drops per day | 10 AM, 7 PM, and (2 PM based on provider assessment) |

Figure 7:
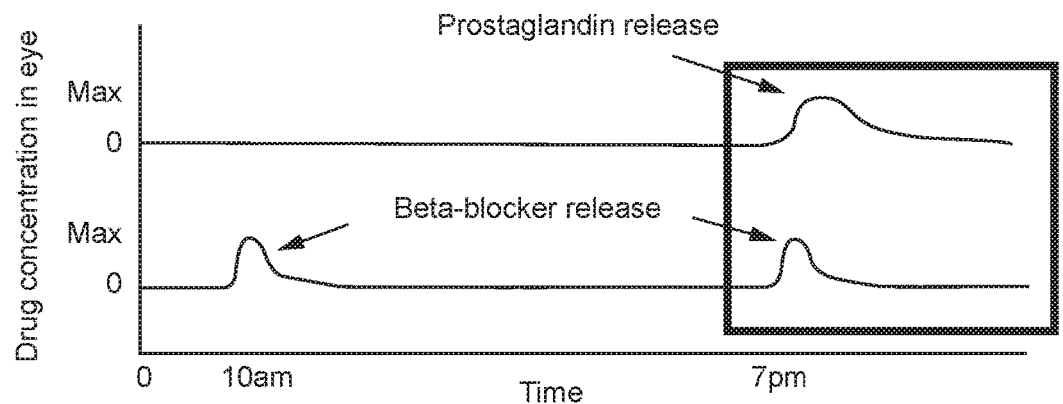
FIG. 7 shows an example of programmed dosage timing executable by the therapeutic agent delivery device for the two agents in accordance with various embodiments.

Additionally or alternatively, customized or programmed release and delivery profiles can be specified for a multi-therapy regimen. Table 2 shows an exemplary bi-therapy regimen for glaucoma. FIG. 7 shows an example of programmed dosage timing executable by the therapeutic agent delivery device for the two agents shown in Table 2. Here the device provides the same recommended dosing regimen that a health care provider would prescribe to a patient with eye-drops. However, it should be clear that while the current clinically recommended scheduling can be delivered, the device may release and deliver at any desired time and at higher frequency if desired. Moreover, the agents may be released simultaneously as depicted in FIG. 7 or they may be staggered in time to allow for independent non-competitive diffusion into the eye. Timing may be staggered by programming +/−1 hr between dosing events for example but is fully customizable to a patient's individual schedule.

TABLE 2

| Drug Class | Recommended Dosing | Exemplary Device Programmed Regimen |
|---|---|---|
| Prostaglandin analogues | One drop per day | 7 PM |
| Beta-blockers | Up to two drops per day | 10 AM and (7 PM based on provider assessment) |

Figure 8:
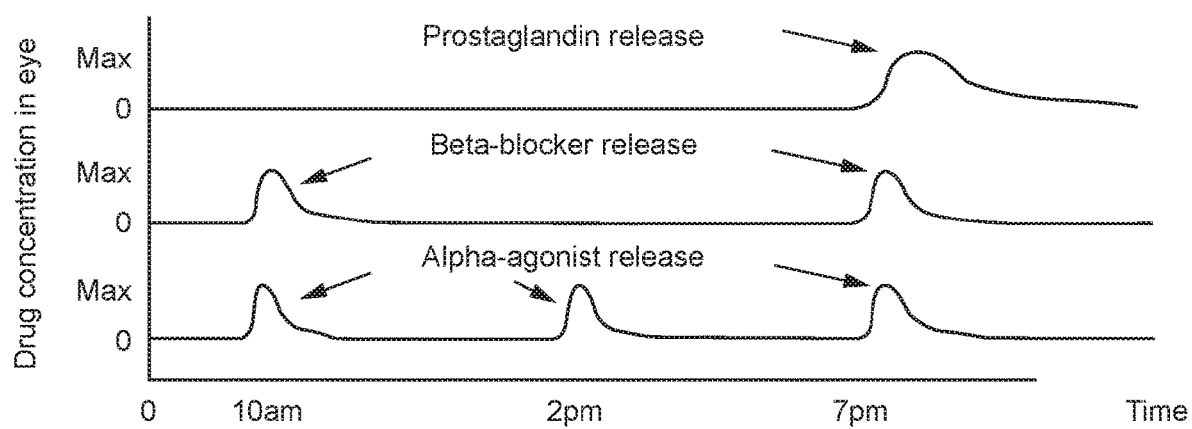
FIG. 8 shows an example of programmed dosage timing executable by the therapeutic agent delivery device for the three agents.

Table 3 shows an exemplary tri-therapy regimen for glaucoma. FIG. 8 shows an example of programmed dosage timing executable by the therapeutic agent delivery device for the three agents shown in Table 3. Here the device provides the same recommended dosing regimen that a health care provider would prescribe to a patient with eye-drops. However, it should be clear that while the current clinically recommended scheduling can be delivered, the device may release and deliver at any desired time and at higher frequency if desired. Moreover, the agents may be released simultaneously as depicted in FIG. 8 or they may be staggered in time to allow for independent non-competitive diffusion into the eye. Timing may be staggered by programming +/−1 hr between dosing events for example but is fully customizable to patient's individual schedule.

TABLE 3

| Drug Class | Recommended Dosing | Exemplary Device Programmed Regimen |
|---|---|---|
| Prostaglandin analogues | One drop per day | 7 PM |
| Beta-blockers | Up to two drops per day | 10 AM and (7 PM based on provider assessment) |
| Alpha-agonists | Two or three drops per day | 10 AM, 7 PM, and (2 PM based on provider assessment) |

As noted herein, the flowcharts of FIGS. 4-6 illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combination of blocks in the block diagrams and/or flowchart illustration, can be implemented by special purpose hardware-based systems that perform the specified functions or acts, or combinations of special purpose hardware and computer instructions.

FIG. 4 depicts a simplified flowchart 400 illustrating a process used by an open control system or open-loop system to provide electronically controlled therapeutic agent release and delivery to enable customized and programmable dosing regimens not possible by traditional passive agent-eluting approaches. In some embodiments, the therapeutic agent delivery is automatically performed by the system without requiring any intervention by the patient or health care provider. These techniques are capable of controlling the timing and rate of therapeutic agent delivery, sustaining the duration of therapeutic activity, and targeting the delivery of a therapeutic agent to a specific region or tissue of the patient. This can eliminate the need for the patient to schedule a subsequent visit to the health care provider for administration of a therapeutic agent or self-administering an agent, thereby providing a convenient route of administration and potentially increasing patient compliance. In these embodiments, the system (e.g., system 200 as described with respect to FIG. 2) may include one or more therapeutic agent delivery devices (e.g., device 100 as described with respect to FIGS. 1A-1C), which includes a polymeric substrate comprising one or more reservoirs, one or more therapeutic agent delivery mechanisms, and a controller.

In step 405, the controller of the therapeutic agent release and delivery system receives a first command signal for the delivery of a therapeutic agent. The first command signal may be received as a wireless or wired command signal or manually by a manipulatable device ("manipulandum") such as a user button. In some embodiments, the first command signal may be received by the controller from a remote device such as a health care provider terminal, a patient controlled device such as a smart phone, a biosensor such as an intraocular pressure sensor, an independent implantable controller, etc. In other embodiments, the first command signal may be received by the controller from an internal component such as an algorithm or data table stored in the controller or memory of the therapeutic agent delivery device. For example, a treatment protocol may be stored in an algorithm or data table, which includes instructions for generating a first command signal to cause the delivery of a therapeutic agent in accordance with a therapy regimen, e.g., a predetermined schedule or table that specifies when a programmed dosing time window is opened/closed.

In step 410, upon receipt of the first command signal, the controller determines whether one or more compliance conditions are satisfied. In some embodiments, the one or more compliance conditions are stored in the controller or memory of the therapeutic agent delivery device. The one or more compliance conditions may include positioning of the device in contact with the target tissue. For example, the controller may determine whether the therapeutic agent delivery device is in contact with the target tissue using a contact sensor. When the one or more conditions are not satisfied (e.g., the device is not positioned on the eye of the patient), the process continues to step 415, where the controller determines whether the dosing time window is still active based on the stored therapy regimen. In some embodiments, the controller may determine whether the dosing time window is still active by comparing a present time to the time boundaries of the dosing time window (e.g., the start and close times) in the stored therapy regimen. When the dosing time window is not still active, the process continues to step 420, where the controller skips delivery of the dosage of the therapeutic agent and records the skip as a negative compliance event. In some embodiments, skipping the delivery of the dosage of the therapeutic agent means that the controller does not initiate a release and delivery protocol to send a signal that releases and delivers the therapeutic agent from one or more reservoirs. Instead, the controller records the skipping of delivery of the dosage of the therapeutic agent as a negative compliance event for compliance tracking purposes. The recording of the negative compliance may be stored in the controller or memory of the therapeutic agent delivery device for record keeping/tracking, and subsequent retrieval and reporting. When the dosing time window is still active, the process return to step 410, where the controller continues to determine whether the one or more compliance conditions are satisfied.

When the one or more conditions are satisfied (e.g., the device is positioned on the eye of the patient), the process continues to step 425, where the controller initiateS a release and delivery protocol that commands the signal generator to generate and send a second command signal causing the capacitor or the one or more circuits to deliver an actuation signal such as a voltage, potential, current, optical signal, or ultrasonic signal causing one or more therapeutic agent delivery mechanisms to open and release the therapeutic agent from one or more reservoirs. In some embodiments, the release and delivery protocol further includes commanding the signal generator to generate and send a third command signal causing the capacitor or the one or more circuits to deliver an actuation signal such as a voltage, potential, current, optical signal, or ultrasonic signal causing the iontophoretic electrode system to deliver the therapeutic agent into a target tissue using an electric field. In some embodiments, the release and delivery protocol commands the signal generator based on the stored therapy regimen. For example, the release and delivery protocol determines the therapeutic agent type and dose to be released in the current dosing time window based on the stored therapy regimen, and commands the signal generator to open reservoirs that store the determined therapeutic agent type and dose and optionally activate electrodes of the iontophoretic electrode system associated with the opened reservoirs to deliver the determined therapeutic agent type and dose into a target tissue using the electric field.

At step 430, the controller records the release and delivery of the dosage of the therapeutic agent as a positive compliance event. In some embodiments, prior to recording the positive compliance, the controller confirms release and delivery of the dosage of the therapeutic agent. The confirming may include receiving an acknowledgment from the signal generator of generating and sending the second command signal and optionally the third command single. Additionally or alternatively, the confirming may include receiving a signal from one or more sensors that detect release and optionally delivery of the dosage of the therapeutic agent. In some embodiments, the controller records the release and delivery of the dosage of the therapeutic agent as a positive compliance event for compliance tracking purposes. The recording of the positive compliance may be stored in the controller or memory of the therapeutic agent delivery device for record keeping/tracking, and subsequent retrieval and reporting. Once the controller records the release and delivery of the dosage of the therapeutic agent, the process returns to step 405, where the controller continues to monitor for other command signals indicative of other dosing time windows being opened/closed.

FIG. 5 depicts a simplified flowchart 500 illustrating a process used by a closed control system or closed-loop system to provide electronically controlled therapeutic agent release and delivery to enable customized and programmable dosing regimens not possible by traditional passive agent-eluting approaches. In some embodiments, the therapeutic agent delivery is automatically performed by the system without requiring any intervention by the patient or health care provider. These techniques are capable of controlling the timing and rate of therapeutic agent delivery, sustaining the duration of therapeutic activity, and targeting the delivery of a therapeutic agent to a specific region or tissue of the patient. This can eliminate the need for the patient to schedule a subsequent visit to the health care provider for administration of a therapeutic agent or self-administering an agent, thereby providing a convenient route of administration and potentially increasing patient compliance. In these embodiments, the system (e.g., system 200 as described with respect to FIG. 2) may include one or more therapeutic agent delivery devices (e.g., device 100 as described with respect to FIGS. 1A-1C), which includes a polymeric substrate comprising one or more reservoirs, one or more therapeutic agent delivery mechanisms, and a controller. In these embodiments, the system further includes one or more sensors that record signals from the target tissue (e.g., a intraocular pressure sensors may record fluid pressure inside the eye, which may be indicative or evaluative of glaucoma or hypertension) and communicates with the system's control system to enable the control system to detect the patient's physiological responses to the therapeutic agent delivery and automatically make adjustments (a closed-looped control system) to the therapeutic agent delivery processes described herein with reduced or no inputs from the patient or health care provider.

In step 505, the controller of the therapeutic agent release and delivery system detects and monitors a physiological parameter via one or more sensors connected to the target tissue. The one or more sensors may be on-board the device, external of the patient, or implanted within the patient. In various embodiments, the detecting and monitoring of physiological parameters includes the measurement and recording of intraocular pressure ($IOP_{actual}$) from one or more intraocular pressure sensors that are in contact with the fluid or tissue of the eye. The controller may record the date and time of all detections and therapeutic agent release and delivery, and stores segments of the data for further analysis and processing. Physiological data recording may be continuous or triggered by detection, responsive stimulation, scheduled time of the day, magnet (used by the patient to indicate an event), and/or other events as programmed by the health care team. The detection algorithms in the therapeutic agent release and delivery system may be computationally efficient and optimized in order to perform real-time detection within the constraints of currently available technology, such as limited power and processing capabilities. In some embodiments, the parameters for the detection algorithms are configurable and may be selected by the health care team to adjust the sensitivity, specificity, and latency of the detection. In certain embodiments, the detection algorithms detect spikes and rhythmic activity occurring in the physiological parameters, identify changes in both amplitude and frequency of the physiological parameters, identify changes in the physiological parameters without regard for frequency, and/or detect changes in physiological parameters depending on time resolution of the physiological parameter measurement data. These detection algorithms are efficient (requiring low computational power), and can be configured to detect physiological events within a fraction of a second or to detect more subtle changes in amplitude, frequency, power, blood flow, inflammation, fluidic pressure, etc. that occur over several seconds.

In step 510, the controller of the therapeutic agent release and delivery system determines whether the detected physiological parameter is abnormal. In various embodiments, target or baseline values for a desired physiological parameters are obtained and recorded for a patient. In some embodiments, the target or baseline values may be obtained from a health care provider and recorded in the controller or memory of the therapeutic agent delivery device. In certain embodiments, the target or baseline values for intraocular pressure ($IOP_{Target}$) are recorded in the controller or memory of the therapeutic agent delivery device. In some embodiments, once monitoring begins on the patient, the values recorded for the physiological parameter may be compared respectively to the target or baseline values to determine the extent of change in the physiological parameter. The determined extent of change for the physiological parameter may then be compared to predetermined threshold values or ranges of values set for the physiological parameter to determine whether abnormal physiology is detected. For example, a physiological parameter such as the intraocular pressure may be determined to be abnormal when the extent of change between the $IOP_{Target}$ and the $IOP_{Actual}$ exceeds or falls below the predetermined threshold value set or remains within our outside of a predetermined threshold value range set, and the intraocular pressure may be determined to be normal when the extent of change between the $IOP_{Target}$ and the $IOP_{Actual}$ is the opposite of abnormal, e.g., falls below or exceeds the predetermined threshold value set or remains within our outside of a predetermined threshold value range set. When the detected physiological parameter is determined to be abnormal, the process proceeds to step 515. When the physiological parameter is determined to be normal, the process proceeds to step 505 to monitor the physiological parameter through-out the remainder of the therapy.

In other embodiments, once monitoring begins on the patient, the values recorded for the physiological parameter may be compared respectively to the target or baseline values to determine a magnitude and direction of deviation error in the physiological parameter. The determined magnitude and direction of deviation error for the physiological parameter may then be compared to predetermined threshold values or ranges of values set for the physiological parameter to determine whether abnormal physiology is detected. For example, a physiological parameter such as the intraocular pressure may be determined to be abnormal when the magnitude and direction of deviation error for the $IOP_{Actual}$ from the $IOP_{Target}$ exceeds or falls below the predetermined threshold value set or remains within our outside of a predetermined threshold value range set, and the intraocular pressure may be determined to be normal when the magnitude and direction of deviation error for the $IOP_{Actual}$ from the $IOP_{Target}$ is the opposite of abnormal, e.g., falls below or exceeds the predetermined threshold value set or remains within our outside of a predetermined threshold value range set. When the detected physiological parameter is determined to be abnormal, the process proceeds to step 515. When the physiological parameter is determined to be normal, the process proceeds to step 505 to monitor the physiological parameter through-out the remainder of the therapy.

In step 515, the controller initiates a release and delivery protocol that commands the signal generator to generate and send a first command signal causing the capacitor or the one or more circuits to deliver an actuation signal such as a voltage, potential, current, optical signal, or ultrasonic signal causing one or more therapeutic agent delivery mechanisms to open and release a therapeutic agent from one or more reservoirs. In some embodiments, the release and delivery protocol further includes commanding the signal generator to generate and send a second command signal causing the capacitor or the one or more circuits to deliver an actuation signal such as a voltage, potential, current, optical signal, or ultrasonic signal causing the iontophoretic electrode system to deliver the therapeutic agent into a target tissue using an electric field. In some embodiments, the release and delivery protocol commands the signal generator based on a stored therapy regimen. For example, the release and delivery protocol determines the therapeutic agent type and dose to be released for a present situation based on the stored therapy regimen, and commands the signal generator to open reservoirs that store the determined therapeutic agent type and dose and optionally activate electrodes of the iontophoretic electrode system associated with the opened reservoirs to deliver the determined therapeutic agent type and dose into a target tissue using the electric field. The present situation is the detection of the abnormal physiological parameter. In some embodiments, the present situation further includes the measured extent of change for the physiological parameter or the measured magnitude and direction of deviation for the physiological parameter, and the release and delivery protocol initiated by the controller may identify the therapeutic agent type and dose to be released specific for the measured extent of change for the physiological parameter or the measured magnitude and direction of deviation for the physiological parameter. Accordingly, the controller is capable of adjusting the dose (amount) and type of therapeutic agent delivered proportional to extent of change for the physiological. parameter or the measured magnitude and direction of deviation for the physiological parameter In step 520, once the therapeutic agent is delivered to the patient, the process proceeds to step 505 to detect and monitor the physiological parameter via one or more sensors connected to the target tissue through-out the remainder of the therapy. The controller may further refine control over the course of hours to days depending on time-resolution of physiological parameter measurement data provided to the system. Optionally, the controller records the release and delivery of the dosage of the therapeutic agent. In some embodiments, prior to recording the delivery, the controller confirms release and delivery of the dosage of the therapeutic agent. The confirming may include receiving an acknowledgment from the signal generator of generating and sending the first command signal and optionally the second command single. Additionally or alternatively, the confirming may include receiving a signal from one or more sensors that detect release and optionally delivery of the dosage of the therapeutic agent. In some embodiments, the controller records the release and delivery of the dosage of the therapeutic agent for tracking purposes. The recording of the delivery may be stored in the controller or memory of the therapeutic agent delivery device for record keeping/tracking, and subsequent retrieval and reporting. Once the controller records the release and delivery of the dosage of the therapeutic agent, the process returns to step 505 to detect and monitor the physiological parameter via one or more sensors connected to the target tissue through-out the remainder of the therapy.

FIG. 6 depicts a simplified flowchart 600 illustrating a process used by a closed control system or closed-loop system to provide electronically controlled multiple therapeutic agent release and delivery to enable customized and programmable dosing regimens not possible by traditional passive agent-eluting approaches. In some embodiments, the multiple therapeutic agent delivery is automatically performed by the system without requiring any intervention by the patient or health care provider. These techniques are capable of controlling the timing and rate of therapeutic agent delivery, sustaining the duration of therapeutic activity, and targeting the delivery of the therapeutic agents to a specific region or tissue of the patient. This can eliminate the need for the patient to schedule a subsequent visit to the health care provider for administration of a therapeutic agent or self-administering an agent, thereby providing a convenient route of administration and potentially increasing patient compliance. In these embodiments, the system (e.g., system 200 as described with respect to FIG. 2) may include one or more therapeutic agent delivery devices (e.g., device 100 as described with respect to FIGS. 1A-1C), which includes a polymeric substrate comprising a plurality of reservoirs, a plurality of therapeutic agent delivery mechanisms, and a controller. In these embodiments, the system further includes one or more sensors that record signals from the target tissue (e.g., a intraocular pressure sensors may record fluid pressure inside the eye, which may be indicative or evaluative of glaucoma or hypertension) and communicates with the system's control system to enable the control system to detect the patient's physiological responses to the therapeutic agent delivery and automatically make adjustments (a closed-looped control system) to the therapeutic agent delivery processes described herein with reduced or no inputs from the patient or health care provider.

In step 605, the controller of the therapeutic agent release and delivery system obtains one or more parameters set by a health care provider. The one or more parameters may include a therapeutic agent treatment hierarchy. The therapeutic agent treatment hierarchy may include various classes of agents (e.g., the classes of drugs shown in Tables 1-3) that are prescribe for treatment or therapy of a disease or condition affecting the patient. The therapeutic agent treatment hierarchy may describe a priority system for the various classes of agents. For example, classes of agents at the top of the hierarchy may take precedence over classes of agents at the bottom of the hierarchy. The one or more parameters may additionally or alternatively include a maximum prescribed daily dosage limit for each class of agent (e.g., the recommended dosing shown in Tables 1-3). The maximum prescribed daily dosage limit may describe a maximum dosage per therapy administration and a maximum dosage per time frame such as per day. The one or more parameters may additionally or alternatively include one or more target profiles for one or more physiological parameters. The one or more target profiles may be provided for one or more physiological parameters that are indicative or evaluative for treatment or therapy of a disease or condition affecting the patient. The one or more target profiles may described the target or baseline values for the one or more physiological parameters (e.g., $IOP_{Target}$). In various embodiments, the health care provider will provide to the controller a therapeutic agent treatment hierarchy that include multiple therapeutic agents, a maximum daily dosage for each therapeutic agent in the therapeutic agent treatment hierarchy, and one or more target profiles for one or more physiological parameters based on the patient's current medical state and treatment goals.

In step 610, the controller detects and monitors one or more physiological parameters via one or more sensors connected to the target tissue based on the one or more parameters obtained in step 605. The one or more sensors may be on-board the device, external of the patient, or implanted within the patient. In various embodiments, the detecting and monitoring of one or more physiological parameters includes the measurement and recording of intraocular pressure ($IOP_{actual}$) from one or more intraocular pressure sensors that are in contact with the fluid or tissue of the eye. The controller may record the date and time of all detections and therapeutic agent release and delivery, and stores segments of the data for further analysis and processing. Physiological data recording may be continuous or triggered by detection, responsive stimulation, scheduled time of the day, magnet (used by the patient to indicate an event), and/or other events as programmed by the health care team. The detection algorithms in the therapeutic agent release and delivery system may be computationally efficient and optimized in order to perform real-time detection within the constraints of currently available technology, such as limited power and processing capabilities. In some embodiments, the parameters for the detection algorithms are configurable and may be selected by the health care team to adjust the sensitivity, specificity, and latency of the detection. In certain embodiments, the detection algorithms detect spikes and rhythmic activity occurring in the physiological parameters, identify changes in both amplitude and frequency of the physiological parameters, identify changes in the physiological parameters without regard for frequency, and/or detect changes in physiological parameters depending on time resolution of the physiological parameter measurement data. These detection algorithms are efficient (requiring low computational power), and can be configured to detect physiological events within a fraction of a second or to detect more subtle changes in amplitude, frequency, power, blood flow, inflammation, fluidic pressure, etc. that occur over several seconds.

In step 615, the controller of the therapeutic agent release and delivery system determines whether the detected one or more physiological parameters are abnormal based on the one or more parameters obtained in step 605. In various embodiments, the target or baseline values for each of the desired physiological parameters are obtained and recorded for a patient (e.g., obtained and recorded in step 605). In some embodiments, the target or baseline values may be obtained from a health care provider and recorded in the controller or memory of the therapeutic agent delivery device. In certain embodiments, the target or baseline values for intraocular pressure ($IOP_{Target}$) are recorded in the controller or memory of the therapeutic agent delivery device. In some embodiments, once monitoring begins on the patient, the values recorded for the physiological parameter may be compared respectively to the target or baseline values to determine the extent of change in the physiological parameter. The determined extent of change for the physiological parameter may then be compared to predetermined threshold values or ranges of values set for the physiological parameter to determine whether abnormal physiology is detected. For example, a physiology such as the intraocular pressure may be determined to be abnormal when the extent of change between the $IOP_{Target}$ and the $IOP_{Actual}$ exceeds or falls below the predetermined threshold value set or remains within our outside of a predetermined threshold value range set, and the intraocular pressure may be determined to be normal when the extent of change between the $IOP_{Target}$ and the $IOP_{Actual}$ is the opposite of abnormal, e.g., falls below or exceeds the predetermined threshold value set or remains within our outside of a predetermined threshold value range set.

In other embodiments, once monitoring begins on the patient, the values recorded for the physiological parameter may be compared respectively to the target or baseline values to determine a magnitude and direction of deviation error in the physiological parameter. The determined magnitude and direction of deviation error for the physiological parameter may then be compared to predetermined threshold values or ranges of values set for the physiological parameter to determine whether abnormal physiology is detected. For example, a physiology such as the intraocular pressure may be determined to be abnormal when the magnitude and direction of deviation error for the $IOP_{Actual}$ from the $IOP_{Target}$ exceeds or falls below the predetermined threshold value set or remains within our outside of a predetermined threshold value range set, and the intraocular pressure may be determined to be normal when the magnitude and direction of deviation error for the $IOP_{Actual}$ from the $IOP_{Target}$ is the opposite of abnormal, e.g., falls below or exceeds the predetermined threshold value set or remains within our outside of a predetermined threshold value range set.

When the detected one or more physiological parameter are determined to be abnormal, the process proceeds to step 620. When the one or more physiological parameters are determined to be normal, the process proceeds to step 610 to monitor the one or more physiological parameters throughout the remainder of the therapy. When multiple physiological parameters are being monitored, in some embodiments, the determination of an overall abnormal or normal status may be determined based on a combination of physiological parameters being abnormal or normal. For example, if two of three physiological parameters are determined to be abnormal then the overall status may be determined to be abnormal. In other embodiments, the determination of an overall abnormal or normal status may be determined based on a combination of physiological parameters and a hierarchical nature of the physiological parameters. For example, if a primary physiological parameter is normal but one secondary physiological parameter is abnormal then the overall status may be determined to be normal; however, if a primary physiological parameter is normal but two secondary physiological parameters are abnormal then the overall status may be determined to be abnormal or if a primary physiological parameter is abnormal but two secondary physiological parameters are normal then the overall status may be determined to be abnormal.

In step 620, the controller obtains a therapy regimen specific for the patient based on the one or more parameters obtained in step 605. The therapy regimen includes therapeutic agent classes, recommended dosing, and dosing time windows. In some embodiments, the therapy regimen is provided by the healthcare provider as the one or more parameters. In other embodiments, the therapy regimen is generated by the controller using the one or more parameters obtained in step 605. In some embodiments, the therapy regimen is a revised therapy regimen that the controller has generated by adjusting therapeutic agent classes, recommended dosing, and/or dosing time windows obtained from an initial therapy regimen received from the healthcare provider. In step 625, the controller determined whether the therapy regimen should be adjusted. In some embodiments, a determination algorithm uses the physiologic parameter data, patient health factors, and personalization factors to generate therapy regimen updates (agent type/combination, agent dosage (amount), and/or timing of dosing) to determine whether the therapy regimen should be adjusted. The health factors may include medications currently taken by the patient, hormone levels, sleep cycle, etc. The personalization factors may include a device wearing schedule, patient travel, patient activity, etc. When the therapy regimen is to be adjusted, the process proceeds to step 630. When the therapy regimen is not to be adjusted, the process proceeds to step 635.

In step 630, the controller adjusts the therapy regimen based on: (i) the one or more parameters obtained in step 605 and (ii) the physiologic parameter data. In some embodiments, the controller adjusts the therapy regimen based on: (i) the one or more parameters obtained in step 605, (ii) the physiologic parameter data, and (iii) the patient health factors, the personalization factors, or a combination thereof. In some embodiments, the controller utilize the additional factors (e.g., the health and/or personalization factors) to apply weights to known drug pharmacokinetic and/or pharmacodynamic behavior. For example, if a patient is overweight, has larger aqueous humor volume, or uses blood thinners the impact of regimen changes to specific drugs can be weighted differently to achieve optimum titration of individual agents. This optimization of the therapy regimen may be accomplished via constrained-optimization algorithms, adaptive neural networks, machine learning optimization or other techniques. It is expected that the system may also interact with external hardware (e.g., a charging station) which will enable off-board processing if required for these optimizations. It should also be understood the frequency of optimization may be dependent on the quantity and frequency of the physical parameter data that the system receives from the one or more sensors. The adjusted or updated therapy regimen is stored in the controller or memory of the therapeutic agent delivery device.

In step 635, the controller initiates a release and delivery protocol that commands the signal generator to generate and send a first command signal causing the capacitor or the one or more circuits to deliver an actuation signal such as a voltage, potential, current, optical signal, or ultrasonic signal causing one or more therapeutic agent delivery mechanisms to open and release at least one therapeutic agent from one or more reservoirs. In some embodiments, the release and delivery protocol further includes commanding the signal generator to generate and send a second command signal causing the capacitor or the one or more circuits to deliver an actuation signal such as a voltage, potential, current, optical signal, or ultrasonic signal causing the iontophoretic electrode system to deliver the at least one therapeutic agent into a target tissue using an electric field. In some embodiments, the release and delivery protocol is selected based on the stored therapy regimen (e.g., an initial therapy regimen or an updated/adjusted therapy regimen). For example, the release and delivery protocol determines the therapeutic agent type and dose to be released for a present situation based on the stored therapy regimen, and commands the signal generator to open reservoirs that store the determined therapeutic agent type and dose and optionally activate electrodes of the iontophoretic electrode system associated with the opened reservoirs to deliver the determined therapeutic agent type and dose into a target tissue using the electric field. The present situation is the detection of the abnormal physiological parameter. In some embodiments, the present situation further includes the measured extent of change for the physiological parameter or the measured magnitude and direction of deviation for the physiological parameter, and the release and delivery protocol initiated by the controller may determine the therapeutic agent type and dose to be released specific for the measured extent of change for the physiological parameter or the measured magnitude and direction of deviation for the physiological parameter. Accordingly, the controller is capable of adjusting the dose (amount) and type of therapeutic agent delivered proportional to extent of change for the physiological. parameter or the measured magnitude and direction of deviation for the physiological parameter In step 640, once the therapeutic agent is delivered to the patient, the process proceeds to step 610 to detect and monitor the one or more physiological parameters via one or more sensors connected to the target tissue through-out the remainder of the therapy. The controller may further refine control over the course of hours to days depending on time-resolution of physiological parameter measurement data provided to the system. Optionally, the controller records the release and delivery of the dosage of the therapeutic agent. In some embodiments, prior to recording the delivery, the controller confirms release and delivery of the dosage of the therapeutic agent. The confirming may include receiving an acknowledgment from the signal generator of generating and sending the first command signal and optionally the second command single. Additionally or alternatively, the confirming may include receiving a signal from one or more sensors that detect release and optionally delivery of the dosage of the therapeutic agent. In some embodiments, the controller records the release and delivery of the dosage of the therapeutic agent for tracking purposes. The recording of the delivery may be stored in the controller or memory of the therapeutic agent delivery device for record keeping/tracking, and subsequent retrieval and reporting. Once the controller records the release and delivery of the dosage of the therapeutic agent, the process returns to step 505 to detect and monitor the physiological parameter via one or more sensors connected to the target tissue through-out the remainder of the therapy.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:

1. A therapeutic agent release and delivery system comprising:
    a therapeutic agent delivery device configured to be positioned on a surface of an eye of a patient to deliver a therapeutic agent to a treatment site of an eye of a patient; and
    a controller, connected to the therapeutic agent delivery device, comprising a non-transitory memory to store data comprising a dosing regimen for the patient, and executable instructions and a processor to access the memory and execute the instructions to at least:
        receive a signal from a sensor comprising an indication of a time;
        consult the dosing regimen to determine whether a dosing time window of the dosing regimen is occurring based on the indication of the time; and
        when the dosing time window is occurring, direct the therapeutic agent delivery device to release a dose of the therapeutic agent to the treatment site; and
        when the dosing window is not occurring, continue operating as normal.

2. The system of claim 1, wherein the therapeutic agent delivery device comprises a signal generator and a therapeutic agent delivery mechanism,
    wherein the signal generator is configured to communicate with the controller and the therapeutic agent delivery mechanism so that when the dosing time window is occurring, the processor further executes the instructions to:
        receive a command signal based on the stored dosing regimen to release the therapeutic agent; and
        direct the signal generator to deliver an actuation signal to the therapeutic agent delivery mechanism to release the therapeutic agent to the treatment site.

3. The system of claim 2, wherein the processor further executes the instructions to direct the signal generator to deliver another actuation signal to an iontophoretic electrode system of the therapeutic agent delivery device to facilitate delivery of the therapeutic agent into a target tissue using an iontophoretic electric field.

4. The system of claim 1, wherein the dosing regimen comprises a type of therapeutic agent and a dose of the therapeutic agent, wherein the processor is further configured to determine at least one delivery profile based on the dosing regimen.

5. The system of claim 4, wherein the dosing regimen comprises at least two types of therapeutic agent, a dose for each of the at least two types of therapeutic agent, and a dosing time window for each of the at least two types of therapeutic agent.

6. The system of claim 5, wherein the dosing time window for each of the at least two types of therapeutic agent are independent.

7. The system of claim 5, wherein the therapeutic agent delivery device comprises a signal generator and a therapeutic agent delivery mechanism,
    wherein the processor is further configured to execute the instructions to:
        direct the signal generator to actuate a therapy delivery mechanism for a first type of therapeutic agent during a dosing time window for the first type of therapeutic agent; and
        direct the signal generator to actuate a therapy delivery mechanism for a second type of therapeutic agent during a dosing time window for the second type of therapeutic agent.

8. The system of claim 1, further comprising another sensor configured to record a physiological signal, wherein the processor further executes instructions to:
    receive the physiological signal from the other sensor;
    determine if the physiological signal is abnormal based on a condition of the dosing regimen;
    when the physiological signal is abnormal, then direct the therapeutic agent delivery device to release the therapeutic agent to the treatment site during the dosing time window; and
    when the physiological signal is not abnormal continue operating as normal.

9. The system of claim 8, wherein the dosing regimen comprises a condition based on at least one of: spikes in rhythmic activity of the physiological signal, a change in both amplitude and frequency of the physiological signal, and changes in the physiological signal depending on time resolution of the physiological signal measurement data.

10. The system of claim 8, wherein the processor further executes instructions to:
    alter a type of therapeutic agent, a dose of the therapeutic agent and/or the dosing time window of the dosing regimen based on the physiological signal.

11. The system of claim 8, wherein the physiological signal comprises intraocular pressure.

12. The system of claim 1, wherein the signal from the sensor triggers the controller to provide a command signal.

13. A method comprising:
    receiving, by a controller of a therapeutic agent release and delivery system comprising a processor, a signal from a sensor comprising an indication of a time, wherein the therapeutic agent release and delivery system further comprises a therapeutic agent delivery device in communication with the controller, configured to store a therapeutic agent, and positioned on an eye of a patient;
    consulting, by the controller, a dosing regimen for the patient stored in a memory of the controller to determine whether a dosing time window of the dosing regimen for the therapeutic agent is occurring based on the indication of the time;
    when the dosing time window is occurring, directing, by the controller, the therapeutic agent delivery device to release a dose of the therapeutic agent to a treatment site on the eye of the patient; and when the dosing window is not occurring, waiting for another signal.

14. The method of claim 13, wherein the directing further comprises:

directing, by the controller, a signal generator of the therapeutic agent delivery device to deliver an actuation signal to a therapeutic agent delivery mechanism of the therapeutic agent delivery device to release the therapeutic agent to the treatment site.

15. The method of claim 14, further comprising:

directing, by the controller, the signal generator to deliver another actuation signal to an iontophoretic electrode system of the therapeutic agent delivery device to facilitate delivery of the therapeutic agent into a target tissue using an iontophoretic electric field.

16. The method of claim 13, wherein the dosing regimen comprises a type of therapeutic agent and a dose of the therapeutic agent, and the method further comprises:

determining, by the controller, at least one delivery profile based on the dosing regimen.

17. The method of claim 16, wherein the dosing regimen comprises at least two types of therapeutic agent, a dose for each of the at least two types of therapeutic agent, and a dosing time window for each of the at least two types of therapeutic agent, and the directing further comprises:

directing, by the controller, a signal generator of the therapeutic agent delivery device to actuate a therapeutic agent delivery mechanism of the therapeutic agent delivery device for a first type of therapeutic agent during a dosing time window for the first type of therapeutic agent; and directing, by the controller, the signal generator to actuate a therapeutic agent delivery mechanism of the therapeutic agent delivery device for a second type of therapeutic agent during a dosing time window for the second type of therapeutic agent.

18. The method of claim 13, further comprising:

receiving, by the controller, a physiological signal from another sensor of the therapeutic agent release and delivery system, wherein the other sensor is configured to record a physiological signal;

determining, by the controller, if the physiological signal is abnormal based on a condition of the dosing regimen;

when the physiological signal is abnormal, then directing, by the controller, the therapeutic agent delivery device to release the therapeutic agent to the treatment site during the dosing time window; and when the physiological signal is not abnormal continue operating as normal.

19. The method of claim 18, wherein the dosing regimen comprises a condition based on at least one of: spikes in rhythmic activity of the physiological signal, a change in both amplitude and frequency of the physiological signal, and changes in the physiological signal depending on time resolution of the physiological signal measurement data.

20. The method of claim 18, further comprising:

altering, by the controller, at least one of a type of therapeutic agent, a dose of the therapeutic agent, or the dosing time window of the dosing regimen based on the physiological signal.

* * * * *